(12) United States Patent
Krause

(10) Patent No.: US 7,169,114 B2
(45) Date of Patent: Jan. 30, 2007

(54) BIOPSY AND DELIVERY DEVICE

(76) Inventor: William R. Krause, 820 Gilliams Mountain Rd., Charlottesville, VA (US) 22903

( * ) Notice: Subject to any disclaimer, the term of this patent is extended or adjusted under 35 U.S.C. 154(b) by 287 days.

(21) Appl. No.: 10/858,112

(22) Filed: Jun. 1, 2004

(65) Prior Publication Data
US 2004/0249278 A1 Dec. 9, 2004

Related U.S. Application Data

(60) Provisional application No. 60/475,891, filed on Jun. 4, 2003, provisional application No. 60/474,691, filed on May 30, 2003.

(51) Int. Cl.
*A61B 10/00* (2006.01)
*A61B 6/00* (2006.01)

(52) U.S. Cl. ...................... 600/564; 600/435

(58) Field of Classification Search ............... 600/564, 600/435, 566; 604/22, 44, 198
See application file for complete search history.

(56) References Cited

U.S. PATENT DOCUMENTS

| | | | | |
|---|---|---|---|---|
| 2,850,007 A | * | 9/1958 | Lingley | 600/567 |
| 4,230,123 A | * | 10/1980 | Hawkins, Jr. | 600/435 |
| 4,270,537 A | * | 6/1981 | Romaine | 604/156 |
| 4,763,667 A | * | 8/1988 | Manzo | 600/563 |
| 5,320,110 A | * | 6/1994 | Wang | 600/566 |
| 5,487,392 A | * | 1/1996 | Haaga | 600/566 |
| 5,492,130 A | * | 2/1996 | Chiou | 600/566 |
| 5,718,237 A | * | 2/1998 | Haaga | 600/564 |
| 5,817,033 A | * | 10/1998 | DeSantis et al. | 600/562 |
| 5,891,052 A | * | 4/1999 | Simmons | 600/573 |
| 5,891,105 A | * | 4/1999 | Mahurkar | 604/195 |
| 5,947,978 A | * | 9/1999 | Holsinger | 606/110 |
| 6,022,324 A | * | 2/2000 | Skinner | 600/566 |
| 6,027,514 A | * | 2/2000 | Stine et al. | 606/159 |
| 6,036,657 A | * | 3/2000 | Milliman et al. | 600/564 |
| 6,039,747 A | * | 3/2000 | Shturman et al. | 606/159 |
| 6,086,607 A | * | 7/2000 | Cragg et al. | 606/213 |
| 6,106,484 A | * | 8/2000 | Terwilliger | 600/568 |

(Continued)

*Primary Examiner*—Max F. Hindenburg
*Assistant Examiner*—Kristin D. Rogers
(74) *Attorney, Agent, or Firm*—Sheldon H. Parker

(57) ABSTRACT

A device and method for the obtaining a tissue biopsy and the delivery of a material to provide hemostatis, therapeutic agents or marker material is described that can be used in conjunction with either an aspiration biopsy or a cutting needle biopsy device. The device has an application chamber through which the biopsy mechanism, either a cutting needle device or aspiration needle, passes through. The mechanism for an aspiration biopsy has a biopsy cannula of constant cross section over its entire length connected to an aspiration and collecting chamber and at least one application channel of constant or varying cross section connected to a dispensing chamber integrally connected with the aspiration chamber. The cutting biopsy mechanism has a mechanical or electromechanical mechanism to rapidly fire a stylet with a biopsy trough into the intended tissue and then fire a biopsy cannula over the stylet to sever and retain tissue that has protruded into the biopsy trough. At least one application channel is formed by a tube centrically slipped over the biopsy cannula wall. To enable the collection of tissue specimens, the distal segment of the application channel forms a close fitting and concentric sheath around the biopsy cannula. The versatility of the invention permits its use in many applications, including, for example, liver biopsies, breast biopsies, laparoscopic surgery, and lymphadenectomy procedures.

18 Claims, 20 Drawing Sheets

U.S. PATENT DOCUMENTS

| | | | |
|---|---|---|---|
| 6,213,957 B1 * | 4/2001 | Milliman et al. | 600/566 |
| 6,355,033 B1 * | 3/2002 | Moorman et al. | 606/33 |
| 6,379,328 B1 * | 4/2002 | Mac Clay | 604/82 |
| 6,434,507 B1 * | 8/2002 | Clayton et al. | 702/152 |
| 6,520,955 B2 * | 2/2003 | Reynard | 606/4 |
| 6,575,965 B1 * | 6/2003 | Fitch et al. | 606/15 |
| 6,702,760 B2 * | 3/2004 | Krause et al. | 600/564 |
| 6,730,042 B2 * | 5/2004 | Fulton et al. | 600/562 |
| 6,911,021 B2 * | 6/2005 | Yang et al. | 604/191 |
| 2001/0005778 A1 * | 6/2001 | Ouchi | 600/564 |
| 2003/0135237 A1 * | 7/2003 | Cragg et al. | 606/213 |
| 2004/0073139 A1 * | 4/2004 | Hirsch et al. | 600/564 |
| 2004/0210160 A1 * | 10/2004 | Fulton et al. | 600/562 |
| 2004/0236211 A1 * | 11/2004 | Burbank et al. | 600/431 |
| 2005/0267416 A1 * | 12/2005 | Mohammed | 604/198 |
| 2006/0079829 A1 * | 4/2006 | Fulton et al. | 604/15 |

\* cited by examiner

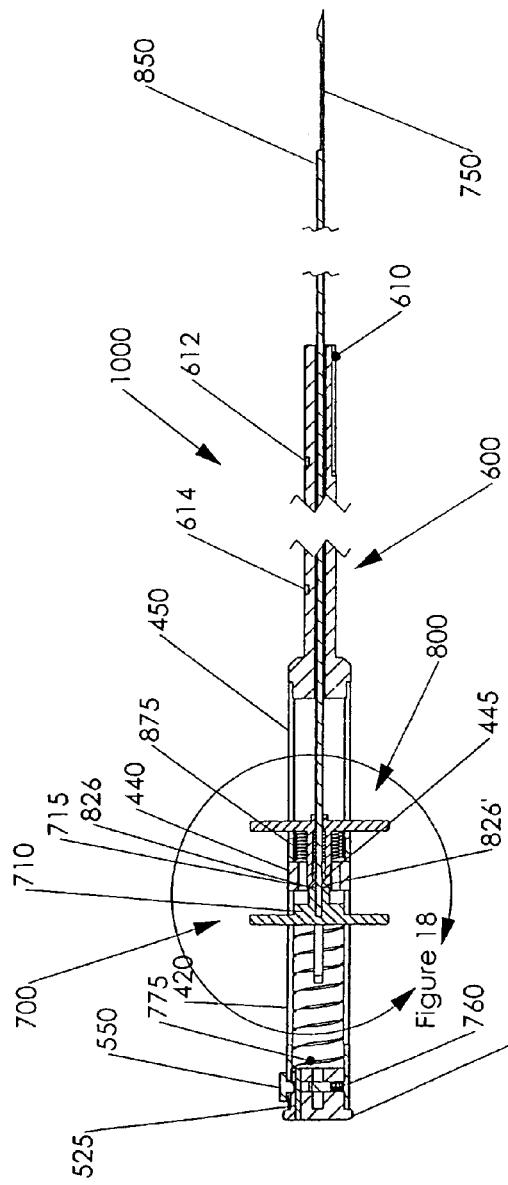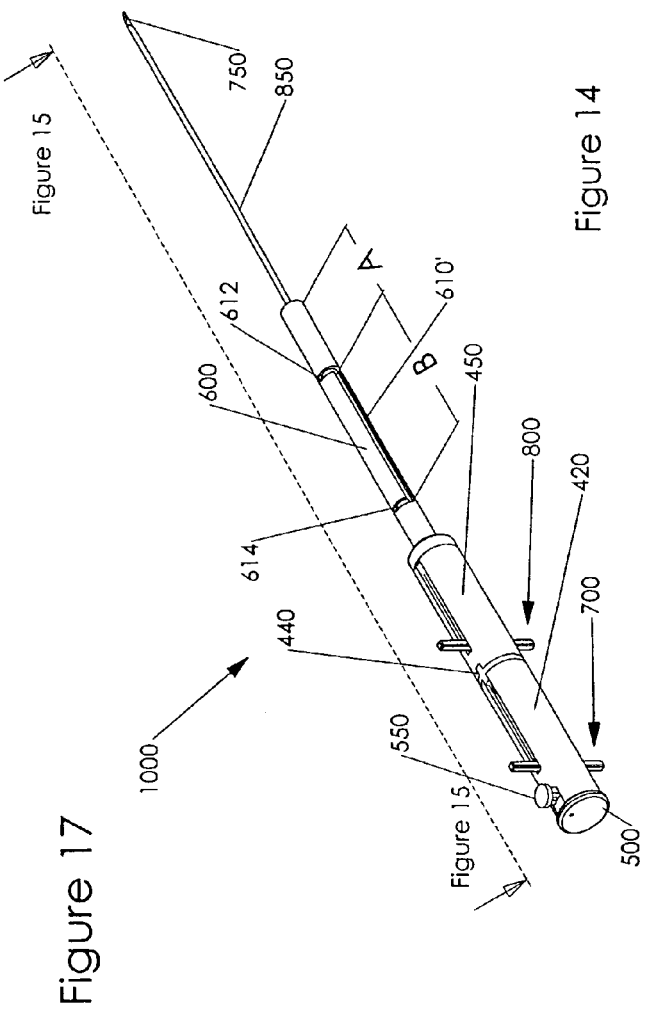

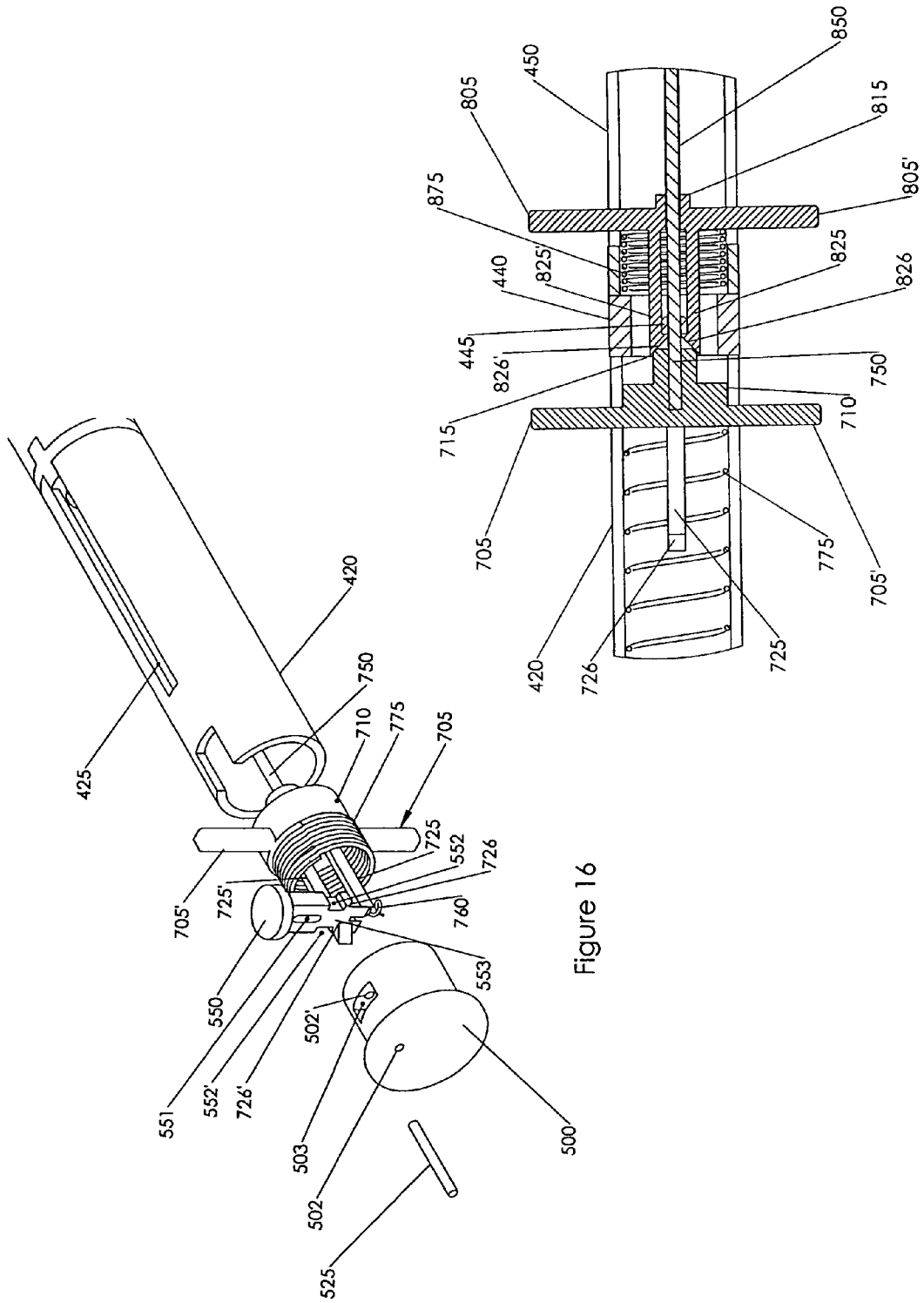

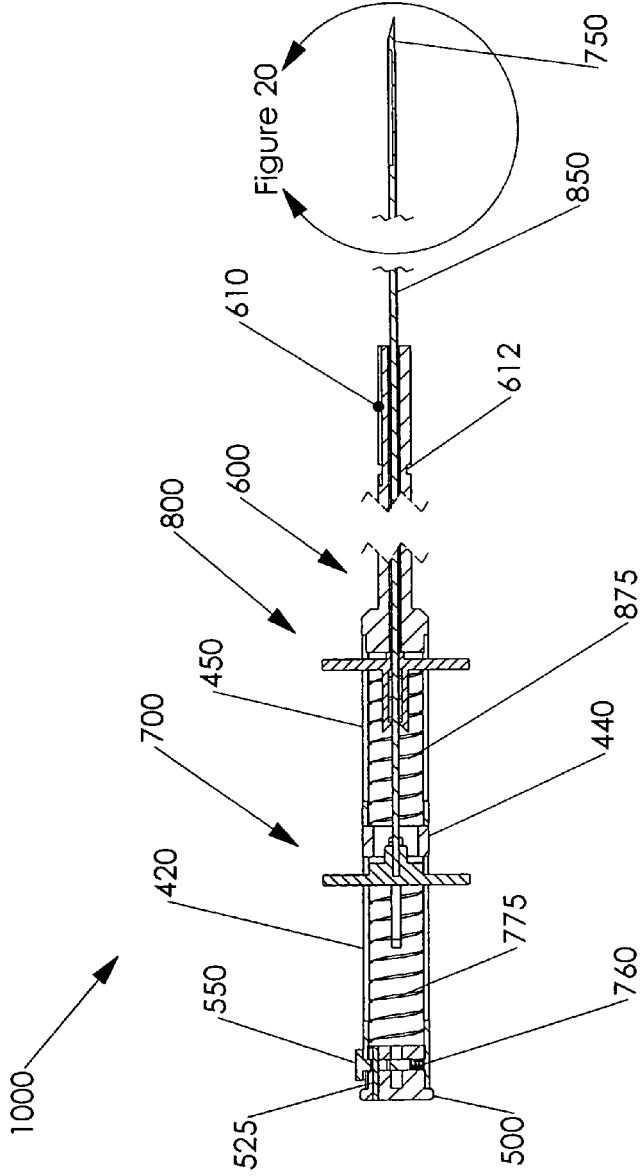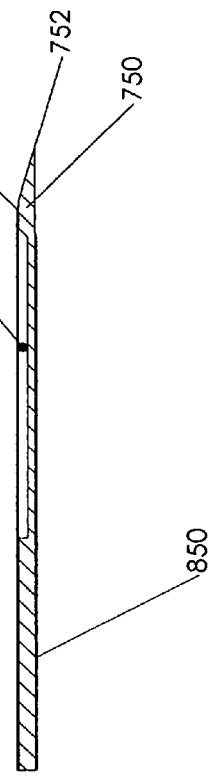
Figure 19
Figure 20

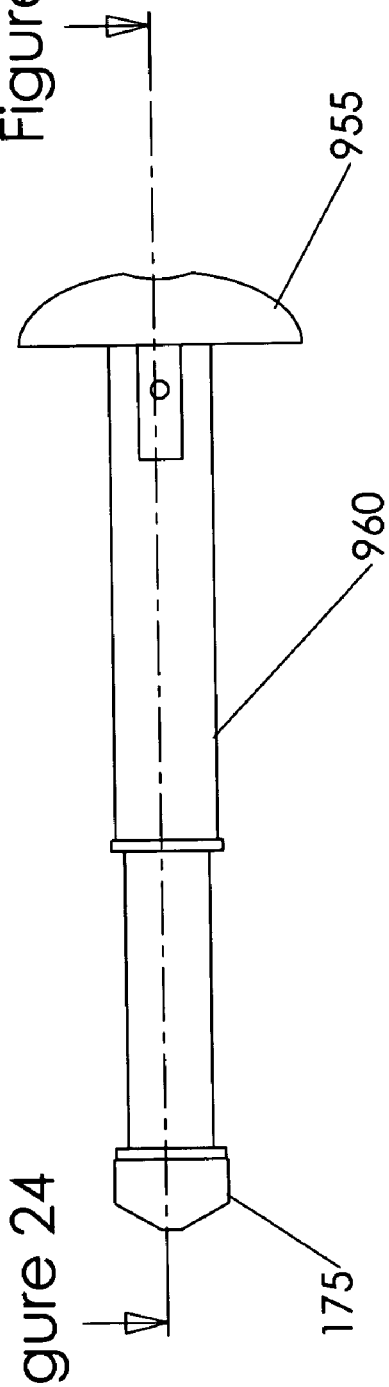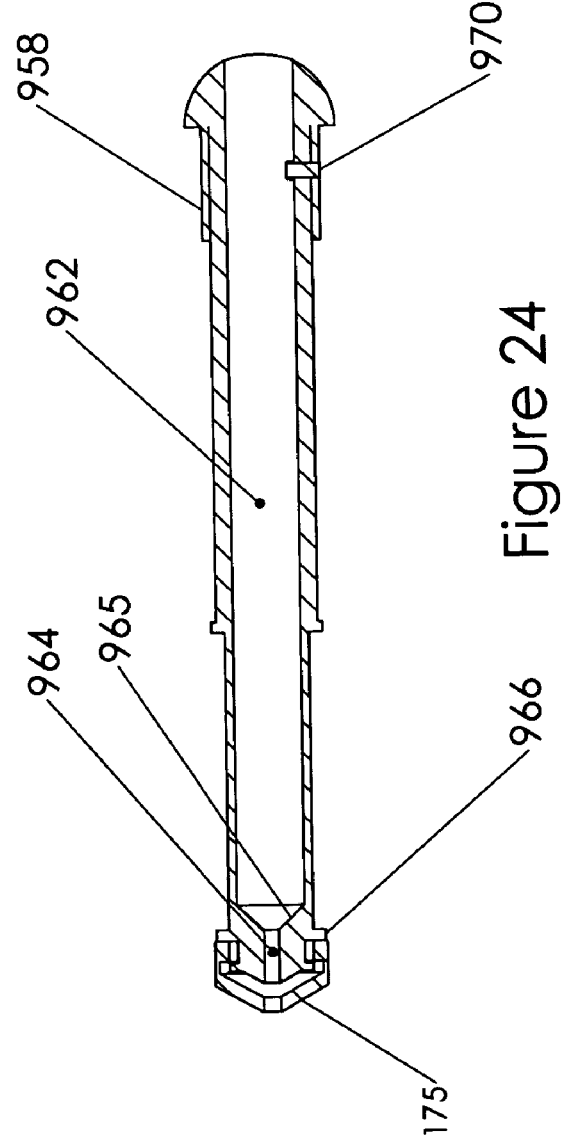

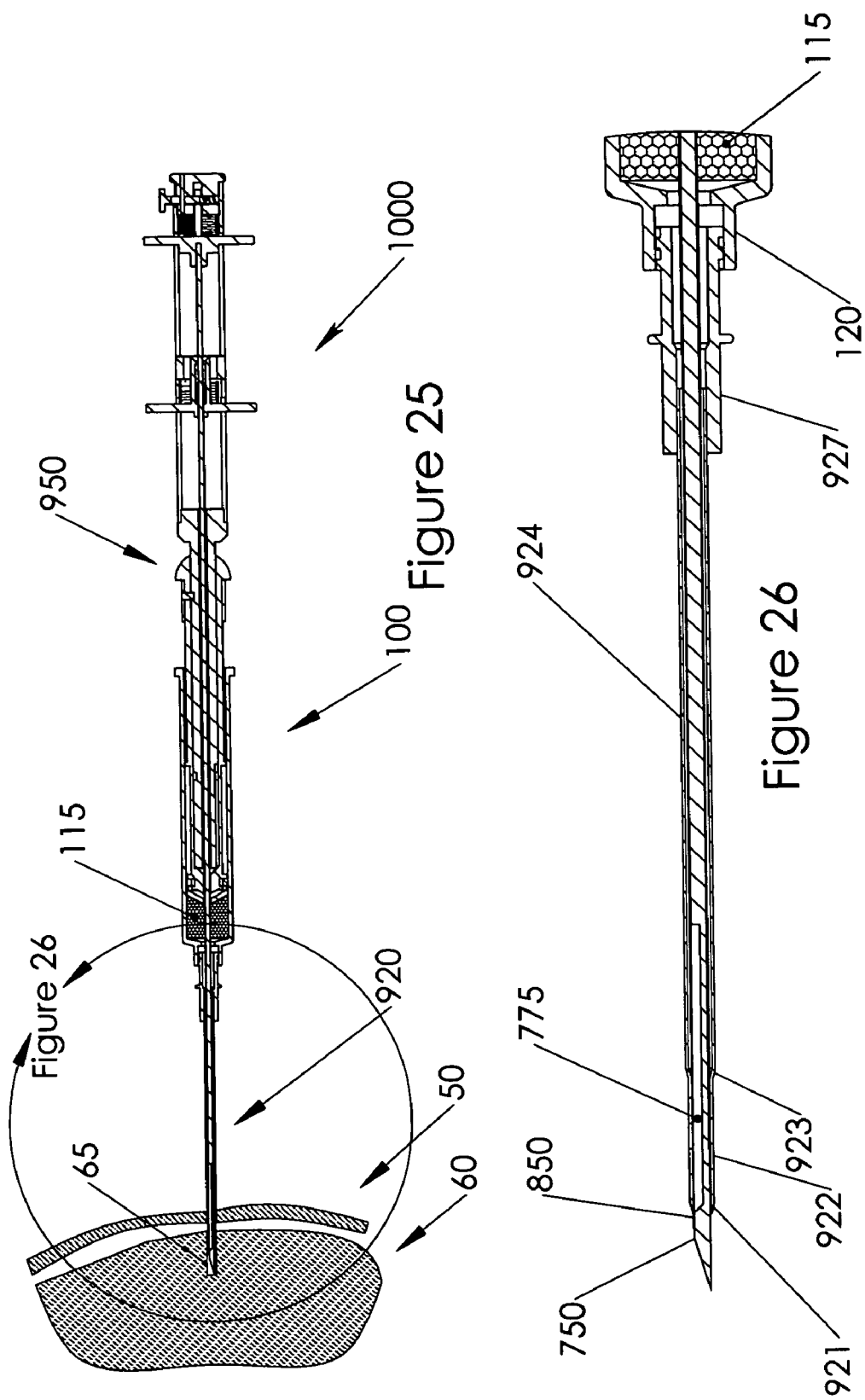

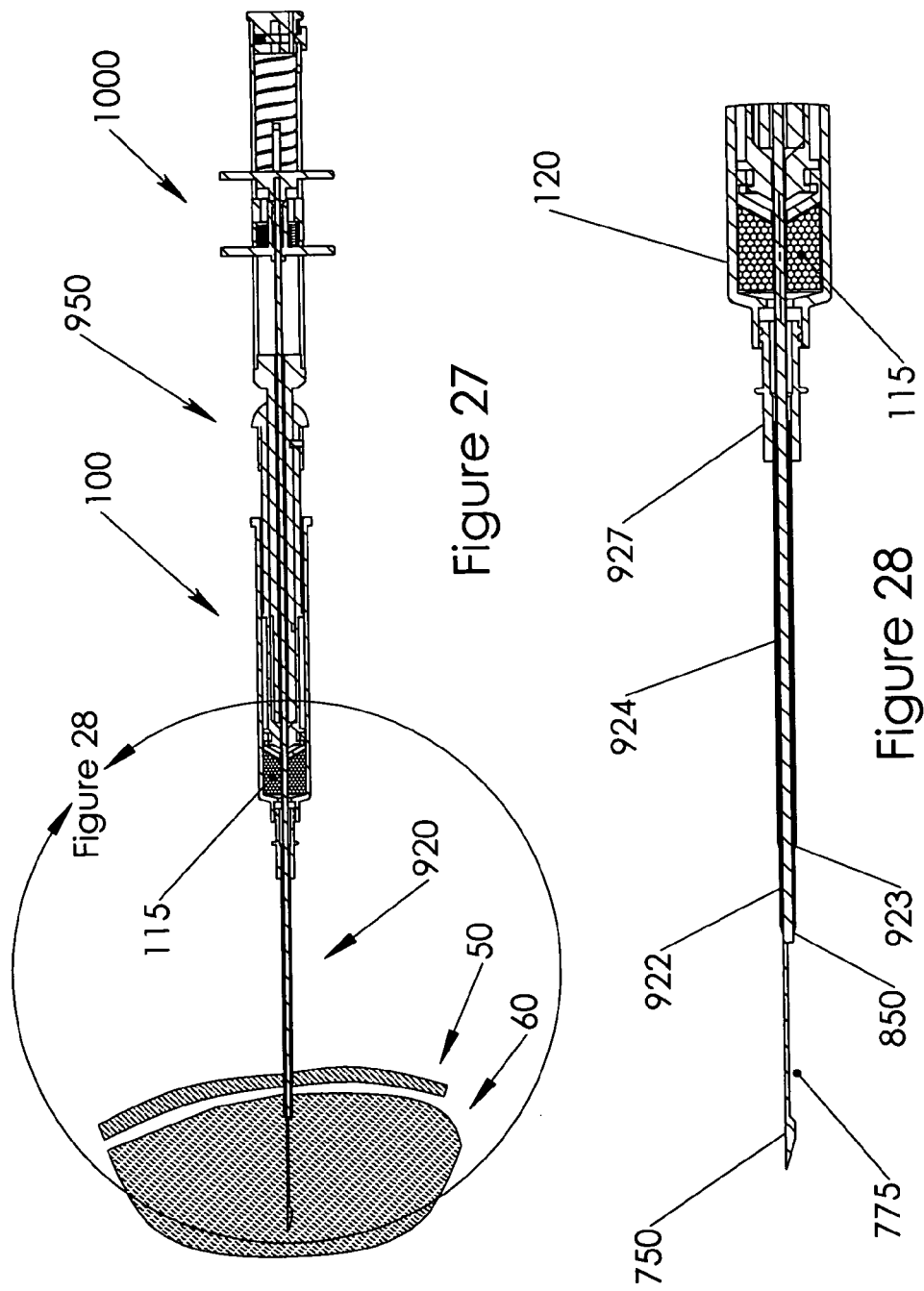

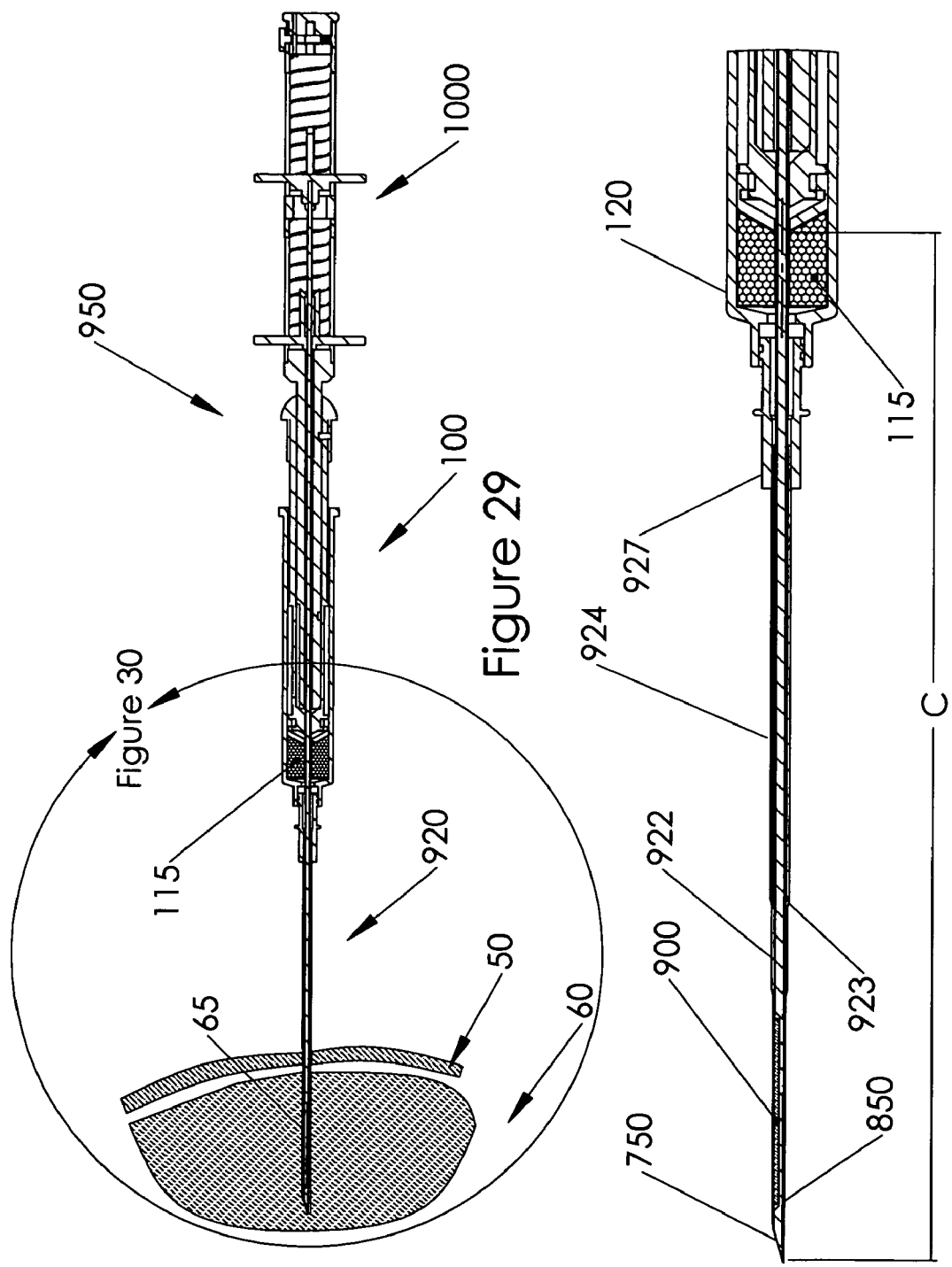

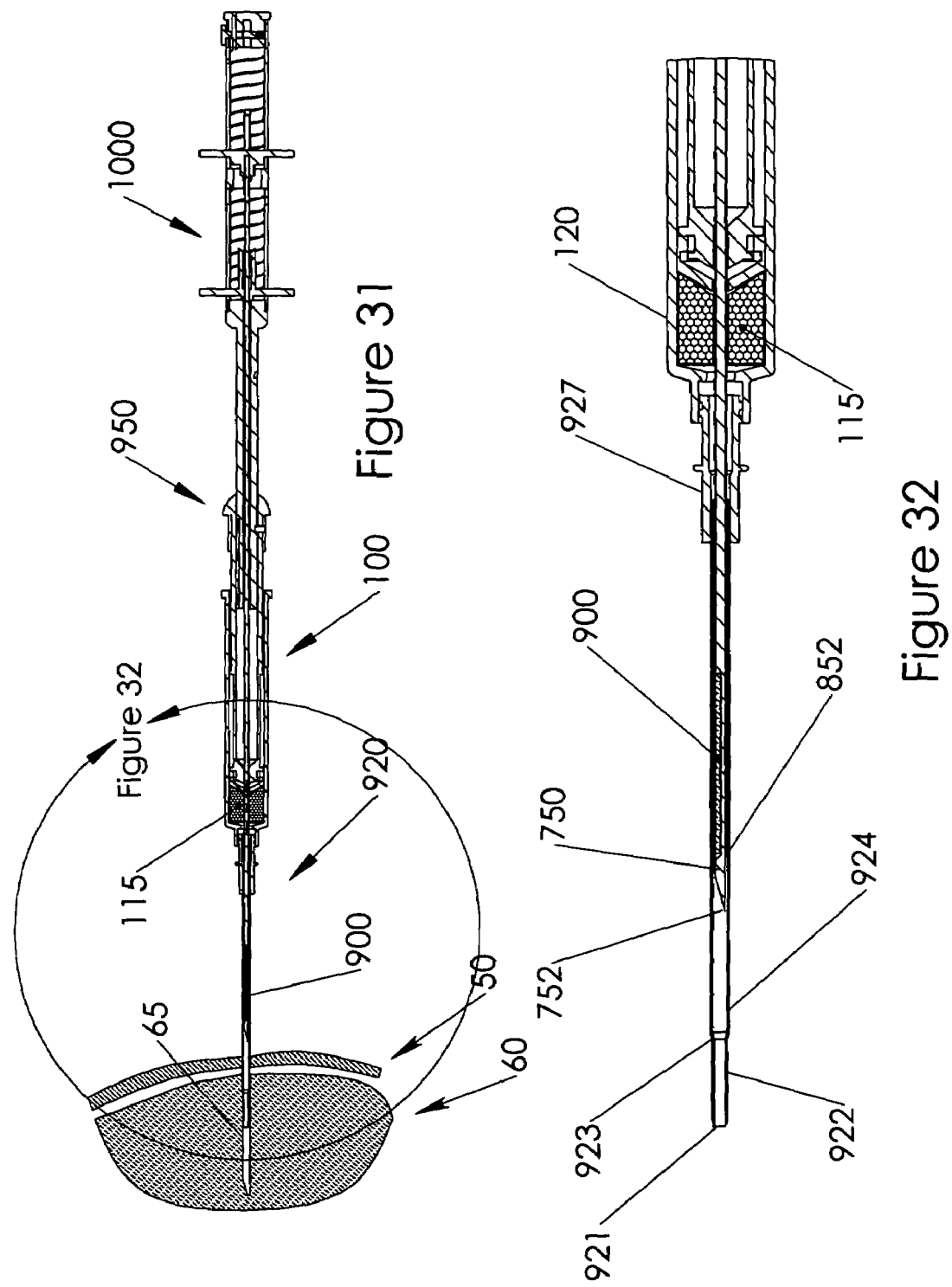

BIOPSY AND DELIVERY DEVICE

CROSS REFERENCE TO RELATED APPLICATIONS

The disclosed application is a conversion of, and takes benefit from, provisional Ser. No. 60/474,691 filed May 30, 2003 and provisional Ser. No. 60/475,891 filed Jun. 4, 2003 to a non-provisional file, the contents of which are incorporated herein as though recited in full.

FIELD OF THE INVENTION

The present invention relates to a biopsy device that takes a biopsy sample of human or animal tissue and delivers a coagulant or other material to the biopsy incision track in order to plug the track and prevent bleeding as well as to provide a marker for future reference so that it can be located in a subsequent medical/surgical procedure.

BACKGROUND OF THE INVENTION

In modern medical practice small tissue samples, known as biopsy specimens, are often removed from tumors, lesions, organs, muscles and other tissues of the body. Such removal of tissue samples can be accomplished by open surgical technique (i.e., removal of a small sample of tissue through a small surgical incision using a local anesthetic), or through the use of a specialized biopsy instrument such as a biopsy needle. After the tissue samples have been removed, they are typically subjected to diagnostic tests or examinations such as a) gross and microscopic examination to determine cytology and/or histology, b) biochemical analyses to determine the presence or absence of chemical substances which indicate certain disease states, c) microbiological culturing to determine the presence of bacteria or other microbes, and/or d) other diagnostic procedures. The information obtained from these diagnostic tests and/or examinations can then be used to make or confirm diagnoses and/or to formulate treatment plans for the patient.

Special Considerations Relating to Biopsy and Plugging the Biopsy Track to Prevent Bleeding; Liver Biopsy Excision biopsy of the liver has traditionally been the gold standard for assessing the extent of injury and determining prognosis in chronic viral hepatitis and liver cancer. A significant complication that frequently occurs is bleeding from the biopsy site. Significant hemorrhage occurs in 0.35 to 0.5% of all procedures while evidence of sub-clinical bleeding, as detectable by ultrasound 24 hours post biopsy, has been reported in up to 23% of patients. A smaller amount of surface bleeding is almost universal and is frequently associated with mild to moderate pain.

Excision biopsies from other organs, such as the lungs, also exhibit a relatively high complication rate due to hemorrhagic incidents and pneumothorax. Also with kidney biopsies and biopsies of other organs, perfuse bleeding is considered the most important complication.

In order to prevent bleeding resulting from the biopsy, it has been proposed to plug the biopsy channel with a hemostatic agent. A typical haemostatic agent can be Gelfoam (Pharmacia & Upjohn), Avitene (Davol, Inc), FloSeal (Fusion Medical Products) or other similar agent. The treatment of a biopsy track with an injectable absorbable coagulant to facilitate homeostasis in conjunction with procuring a biopsy provides substantial advantages in comfort over external pressure methods or the insertion of a pledget of Gelfoam foam as described in U.S. Pat. No. 6,086,607, which must be inserted through a catheter previously inserted. The insertion of a catheter involves a longer procedure and the risk of the catheter shifting while the operator switches or disconnects from the aspiration biopsy syringe to the coagulant delivery syringe. In addition, the present invention also provides advantages over the insertion of an absorbable sponge material in a dry state with an applicator. A dry piece of sponge material must be cut to the particular size of the biopsy track and does not swell to fill the track until the blood has sufficiently saturated the sponge material which can take significantly longer and provides inadequate local compression.

Aspiration Technique

The most common liver biopsy technique is by percutaneously inserting a needle into the liver for a fraction of a second and obtaining a tissue sample. The subsequent procedure for taking the biopsy varies according to whether the biopsy needle is of the aspiration or cutting type. The aspiration technique is probably the most widely used technique with the best known aspiration biopsy technique based on the principle indicated by Menghini. There a hollow needle having an average diameter of 1.4 mm and having a facility for attachment of a syringe is used, by which a negative pressure (suction) is applied upon piercing through the skin and prior to the organ puncture proper. The organ puncture (liver) then is realized with a sustained suction within a second.

In order to obviate the reported complications, it was recommended to subsequently plug the needle track with resorbable material so as to eliminate, in particular, bleeding complications. Such techniques, however, imply a long residence time of the puncture needle in the organ, which again constitutes a cause of complications, in particular with liver punctures.

From Austrian Pat. No. 384,165, a biopsy needle device of the initially defined kind is known, with which the cannula has a curved partition wall towards the internal limitation of the cannula lumina. Therein, the partition wall does not reach immediately to the front end of the cannula so that the biopsy channel and the application channel communicate in the region of the tip of the cannula. The multi-lumen biopsy device according to Austrian Pat. No. 384,165 enables the collection of tissue and the application of substances plugging the puncture track in coordination with the puncturing procedure in one operating cycle, thus largely shortening the time of intervention.

U.S. Pat. No. 4,850,373 and related EP patents 243341 A, B1 etc., also describes a biopsy needle device having a two lumen cannula, a biopsy channel of constant cross section and one application channel. The application channel is formed by a tube eccentrically slipped over the biopsy channel wall. Furthermore, the biopsy channel is described as a non-circular tubular structure with its channel wall flattened in cross section such that an application channel is formed between the flattened side of the biopsy channel wall and the outer application tube. In addition, surface contact exists between the non-flattened side of the biopsy channel wall and the application tube.

A common surgical material used to control bleeding is Gelfoam®, which is supplied in either a powder form or as an implantable sponge. Sterile sponges, such as Gelfoam®, are prepared in dry sterile sheets that are used as packing material during surgery for control of bleeding. The sponge sheets are left in the surgical site after surgery to stop bleeding and are absorbed by the body in 1 to 6 weeks. A number of techniques have used these absorbable sterile sponge materials to plug a biopsy track to minimize or prevent bleeding. The absorbable sponge provides a mechanical blockage of the track, encourages clotting, and minimizes bleeding though the biopsy track. Despite the advantages of using absorbable sponge to plug a biopsy track this technique has not achieved widespread use because of difficulty in preparing and delivering the sponge material into the biopsy track.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the track preventing further bleeding at the biopsy site. However, the sponge is difficult to deliver and expands slowly once delivered. In addition, this delivery method can only deliver a sponge of a limited size that provides less local compression than desired and may incompletely fill the target site. Further, bleeding may continue along sections of the biopsy track where no sponge has been delivered.

Another example of a Gelfoam® inserting device to facilitate hemostasis is described in U.S. Pat. No. 6,086,607. According to this patent, a method of cutting a piece of Gelfoam® sponge from a sheet of the material, folding the strip to form a pledget with one end of different cross section than the other end, and inserting the pledget in an adapter to compress the pledget and for attachment to a syringe for delivery of the pledget to the tissue. The adapter is attached to a cannula that was previously inserted into the organ being biopsied and the Gelfoam® is inserted into the tissue through the cannula.

Cutting Needle Technique

Many cutting biopsy surgical appliances are currently known. Typically, the instrument consists of a long, thin probe, termed a stylet, within a close-fitting hollow needle, termed a cannula. The stylet and cannula are contained within a firing device that first projects the stylet into the tissue, followed immediately by the cannula. The stylet has a notch into which tissue will prolapse when the stylet enters the tissue. As the cannula slides over the stylet, a small piece of tissue is then severed from the organ mass and captured within the notch of the stylet. The instrument is then withdrawn and the piece of tissue removed from the stylet for evaluation.

Griffith, U.S. Pat. No. 3,477,423, was one of the first to describe an economical and simplified, biopsy needle device in which a cannula is projected forward over the stylet with a recessed collection notch such that the tissue within the notch is severed and retained within the cannula for retrieval. Improvements over the years have lead to single handed, semi automatic driving devices as described by U.S. Pat. No. 4,944,308, U.S. Pat. No. 5,368,045 and U.S. Pat. No. 5,951,489.

Special Considerations Relating to Biopsy and Delivering a Marker Material: Breast Biopsy Breast cancer is presently the most common cancer in women and is the second leading cause of cancer deaths in women. Periodic physical and radiographic examination of the breasts (mammography) is important for early detection of potentially cancerous lesions in women over 40 years of age. In mammography, the breast is compressed between two plates while specialized x-ray images are taken. If an abnormal mass in the breast is found by physical examination or mammography, ultrasound may be used to determine whether the mass is a solid tumor or a fluid filled cyst. Cystic lesions are generally benign and the diagnosis of a cystic lesion is often confirmed by needle aspiration of fluid from the interior of the cyst and immediate diagnosis. However, solid masses are usually subjected to some type of tissue biopsy to determine if the mass is cancerous. This determination requires that the tissue be processed which may require 24 to 48 hours.

Therefore in order to locate the site of the biopsy and cancerous tissue for removal or radiographic treatment at a subsequent procedure, the site is marked, either externally or internally, with a biopsy site marker. Various types of biopsy site markers have been known in the prior art. U.S. Pat. No. 2,192,270 (Carswell, Jr.) and U.S. Pat. No. 5,147,307 (Gluck) describes externally applied markers. Additionally, the prior surgical procedures have included radiographically visible markers that may be introduced into the biopsy site such as marker wires that are inserted through the biopsy needle after a tissue sample is removed and are thereafter allowed to remain protruding from the patient's body. U.S. Pat. No. 6,161,034 (Burbank) describes various chemical preparations and methods for marking biopsy sites which remain present and detectable for up to 5 to 8 months from the initial biopsy. A method for simultaneously taking the biopsy sample and delivering the marker material is not described.

The disclosed device overcomes the forgoing problems by teaching the combination of the multi lumen, concentric needle device providing a biopsy channel and an application channel with a syringe assembly for obtaining the biopsy and delivering the application material. The prior art does not describe the combination of a cutting needle biopsy device with a syringe application device for delivery of the application material. In addition, the prior art does not describe an aspiration biopsy needle that translates within the application tube so that the application material will have an unobstructed passage into the biopsy track. The previous patents either describe the biopsy channel as being eccentrically positioned within the application tube as opposed to the disclosed concentric positioned biopsy or a separate device which delivers a hemostatic sponge or marking material to the biopsy track.

SUMMARY OF THE INVENTION

The present invention provides a biopsy device with a view to enabling the collection of tissue specimens for biopsy and to apply auxiliary substances directly in the site of the puncture without tissue specimens getting into the application cannula, thus obstructing the same, or having to change instrumentation.

In accordance with one aspect of the present invention, a syringe system comprised of a multi-chambered unit for taking the biopsy specimen and delivering a coagulating or marker material is described. The system includes a multi-syringed structure with at least one biopsy mechanism for obtaining a biopsy specimen either by using the aspiration needle technique, FIG. 1 or the cutting needle technique, FIG. 21.

The disclosed device is formed by a syringe tube a and application channel formed by a tube of varying or constant cross section slipped over the biopsy mechanism channel wall. The biopsy mechanism is typically positioned within the plunger of the coagulant syringe 100 with the biopsy needle passing through the inner end of the plunger, the seal, coagulant chamber and the application channel. The application channel can also contain separate channels for fiber optic cables for the transmission of light or laser energy used in the photo initiation of delivered material.

Using a commercially available biopsy device, a biopsy is achieved according to the invention in that after the tissue specimen is collected in the biopsy channel of the biopsy needle, the inner tube containing the tissue specimen is retracted within the concentric outer application tube thus allowing the application material to be injected into the biopsy track without obstruction. After obtaining a biopsy, the biopsy syringe is retracted within the application syringe plunger that is depressed by which the application material is expelled from the application chamber into the biopsy site. This may be facilitated according to the invention by a placing the biopsy device in another device that causes the translations and movements of the parts of the fore mentioned biopsy device.

BRIEF DESCRIPTION OF THE DRAWINGS

FIG. 14 is an overall view of the cutting needle device;

FIG. 16 is a detailed, section view of the distal end of the cutting needle device showing the trough formed within the stylet and sheath;

FIG. 17 shows the cutting needle in the initial fired position whereby the stylet mechanism has been released by the button and is impacting the sheath holder. The distal end of the stylet is protruding out from the sheath;

FIG. 18 shows a close up of the sectional view of the stylet mechanism striking the holding arms to disengage the holding arm from the cross arm to release the sheath mechanism;

FIG. 19 is a cutaway view of the cutting device after the device has been activated such that the sheath has extended fully to enclose the specimen trough;

FIG. 20 is a close up of the distal end of the cutting needle depicting a biopsy specimen retained within the specimen trough after the sheath was fired over the stylet;

FIG. 23 shows the application plunger comprised of a handle, a barrel and distal end on which a plunger seal is attached;

FIG. 24 is a sectional view of the plunger;

FIG. 25 is a sectional view of the complete device in the loaded position and inserted through the chest wall into an organ for a biopsy;

FIG. 26 shows the stylet and stylet sheath passing through the application sheath and extending distally from the application sheath tip;

FIG. 27 shows the complete device in the transition stage of activation whereby the stylet has advanced into the organ allowing the tissue to protrude into the trough;

FIG. 28 is close up of the distal end of the complete device showing the extension of the stylet from the application sheath;

FIG. 29 shows the complete device after the device has been fully activated and the stylet sheath has extended over the stylet and the specimen captured within the trough;

FIG. 30 is a close up of the distal end of the device showing the extension of the stylet and sheath with the entrapped biopsy specimen;

FIG. 31 shows the cutting device retracted from the application plunger resulting in the retraction of the stylet and stylet sheath from the biopsy tract;

FIG. 32 is a close up of the application sheath showing the stylet and stylet sheath retracted past the application sheath restriction;

FIG. 37 is a section view through the alternative catch and release mechanism.

DETAILED DESCRIPTION OF THE PREFERRED EMBODIMENTS

The system of the present invention collects and retrieves a biopsy specimen and then delivers, with or without removal of the biopsy assembly, an application material to facilitate hemostasis of the biopsy track or other puncture wound in a simple and safe manner. The delivered application material can also be used to provide a marker for subsequent procedures such as radiation or surgical treatments. The apparatus for collecting the biopsy specimen and delivering a coagulant material will be described below in connection with procurement of a liver biopsy sample for the diagnosis of certain liver diseases. However, the invention can be used for the procurement of other biopsy specimens from other vascular organs as well as facilitating hemostasis of other types of puncture wounds or tissue access tracks to prevent bleeding of these wounds. The invention can also be used for the procurement of a biopsy specimen and the delivery of a marker, therapeutic or other substance into the biopsy site.

The current means of obtaining a biopsy specimen from the liver are either using the aspiration technique or the cutting needle technique. The aspiration technique utilizes a common syringe and 15 to 18 gauge needle for obtaining the biopsy by the technique described by Menghini and Jamshidi. Briefly, the needle is inserted to the surface of the organ to be biopsied, penetrating slightly, suction is applied to the syringe and the needle is then advanced into the organ while maintaining suction. The needle is withdrawn from the body and the specimen flushed from the needle. In another means, a cutting needle is inserted into the organ and the mechanism activated causing a stylet with a specimen trough to penetrate deeper into the tissue. This is followed by a cutting sheath moving outward over the stylet to cut and entrap the tissue that had protruded into the trough. The needle is then withdrawn from the body and the specimen retrieved. A complication with either technique is that after removal of the biopsy device, the tissue bleeds from the resulting biopsy tract. In the liver, the biopsy site will typically bleed up to 5 minutes however, if a major artery within the liver is hit, the bleeding can be severe requiring immediate operative intervention. The invention described forthwith provides a means to take the biopsy specimen and deliver a haemostatic agent to minimize the bleeding from the biopsy tract.

Figure 1:
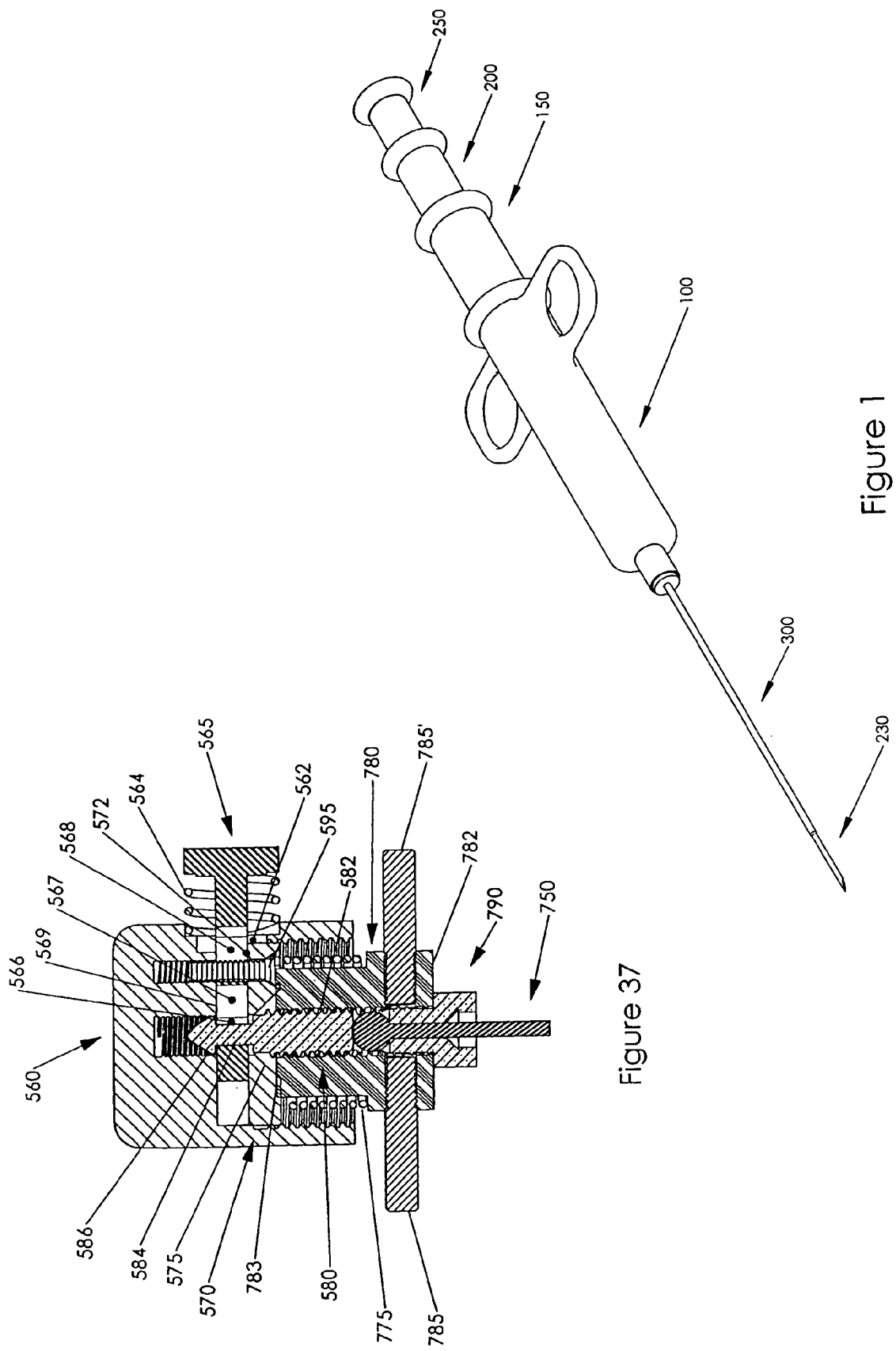
FIG. 1 is an overall view of the assembled biopsy (aspiration syringe) device according to the invention.

FIG. 1 illustrates the assembled aspiration biopsy device 10 of the invention including the application syringe assembly barrel 100, application plunger 150, biopsy syringe barrel 200, biopsy plunger 250, application sheath 130 and the distal tip of the aspiration needle 230 extending beyond the application sheath 130. The individual components of the aspiration syringe are illustrated in FIGS. 2 through 9 and FIGS. 10 through 13 depicting the typical procedural steps of the application of the device in obtaining a biopsy.

Figure 2:
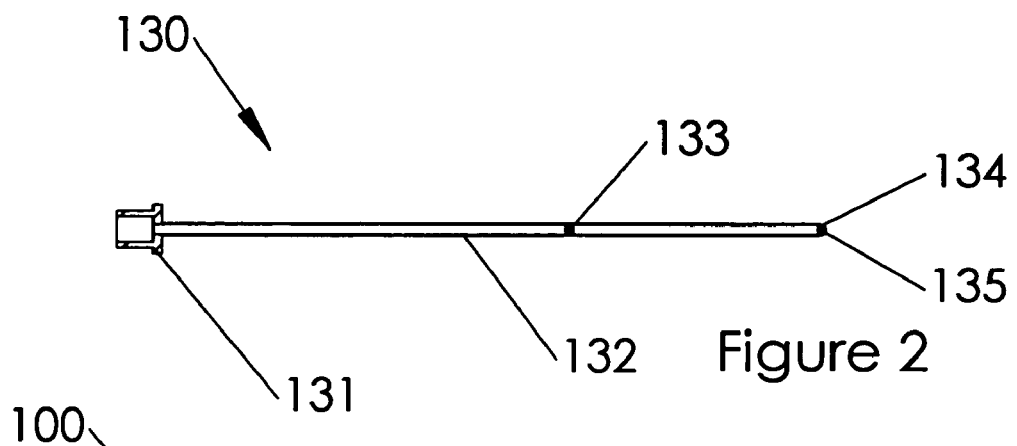
FIG. 2 is a section view of the application sheath.
Figure 3:
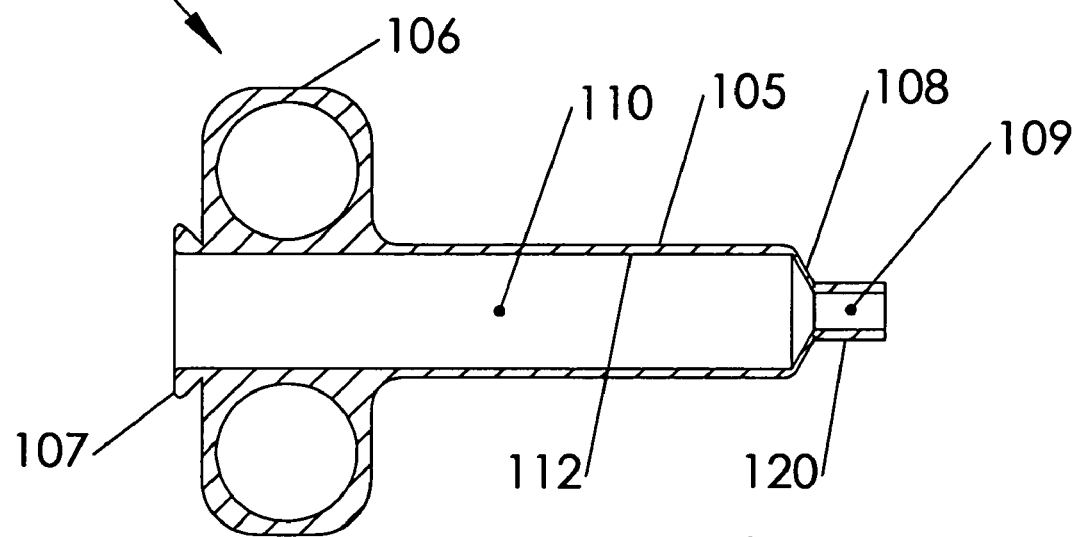
FIG. 3 is a section view of the application syringe body.

The apparatus of the first embodiment of the present invention is illustrated broken down into its individual parts in FIGS. 2–9. As seen in FIG. 2, the application sheath 130 consists of a cannula 132 having an application channel 133 with an open distal end 135 and proximal hub 131. The proximal hub 131 is dimensioned for connection to the application syringe barrel 100 at the distal end connector 120 illustrated in FIG. 3. The application syringe assembly 100 shown in cross section in FIG. 3 has a cylindrical body 105 terminating at a truncated distal end wall 108 integral with a distal connector hub 120. The proximal end of the application syringe assembly 100 has optional finger grips 106 and lip 107 for ease of use.

Figure 4:
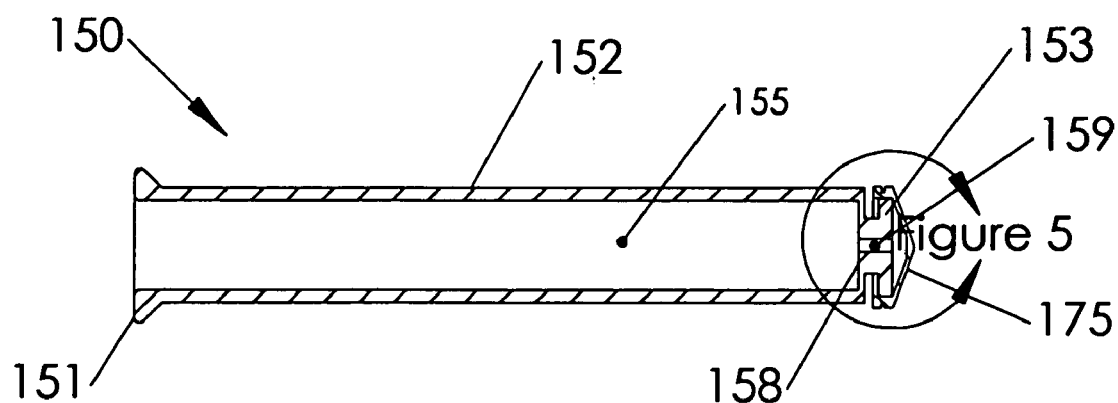
FIG. 4 is a section view of the application plunger.
Figure 5:
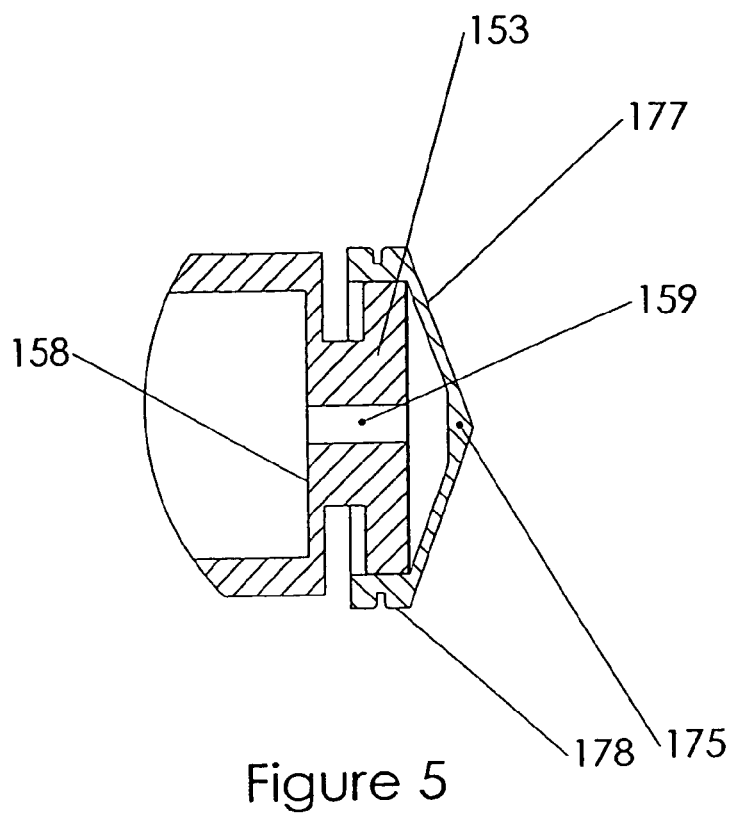
FIG. 5 is a section view of the distal end of the application plunger 150 showing the plunger seal.
Figure 9:
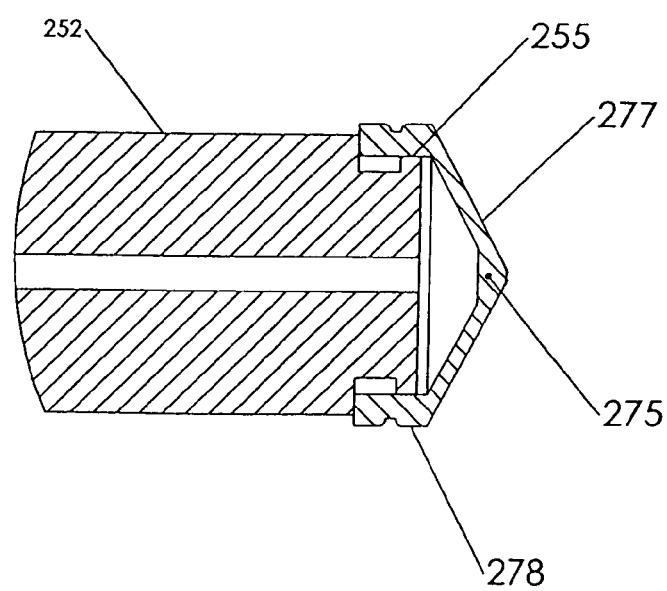
FIG. 9 is a section view of the distal end of plunger 250 showing the plunger seal.
Figure 6:
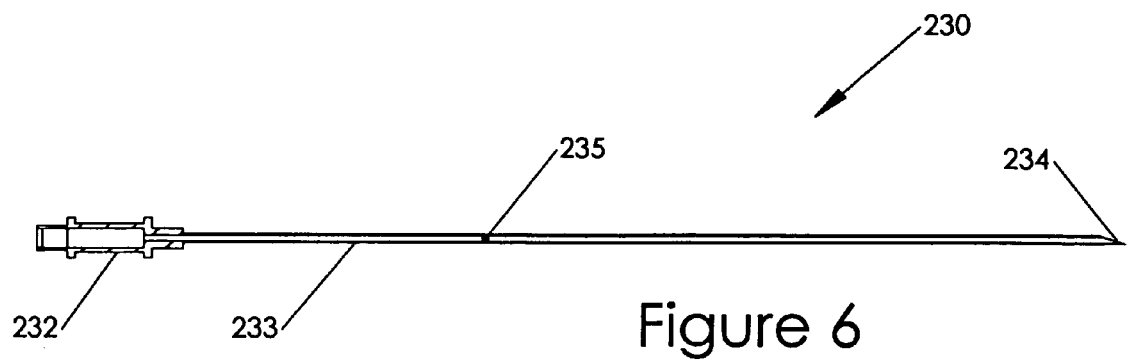
FIG. 6 is a section view of the aspiration needle.
Figure 7:
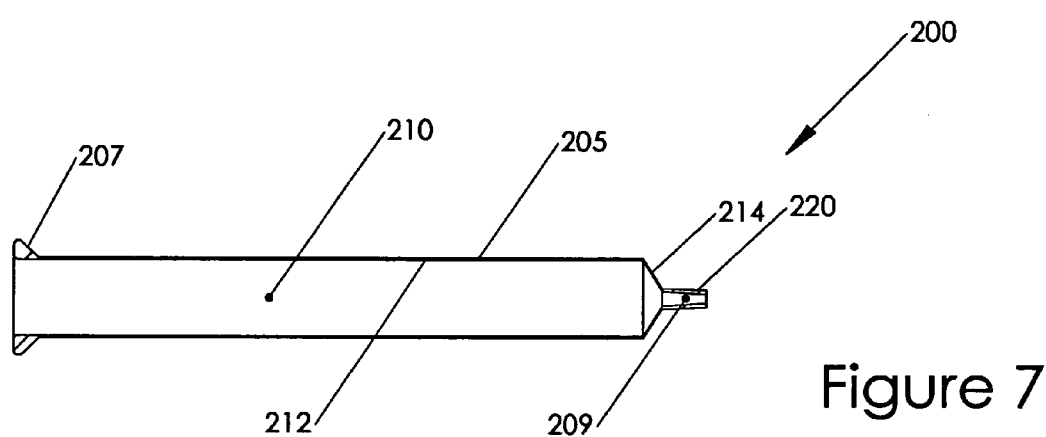
FIG. 7 is a section view of the aspiration syringe body.
Figure 8:
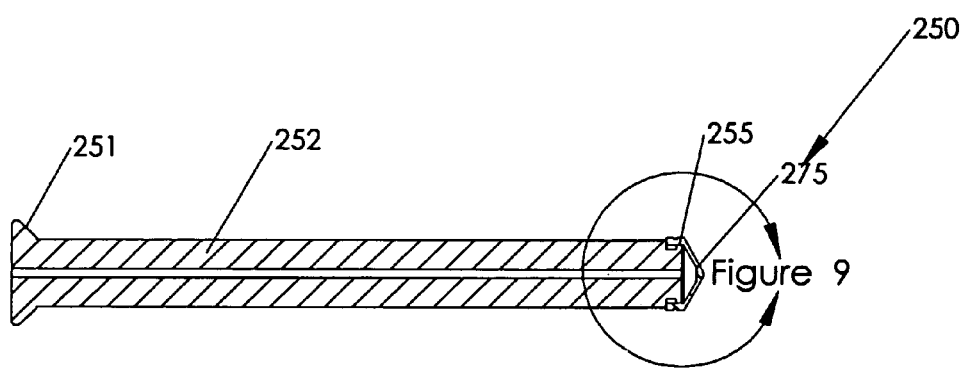
FIG. 8 is section view of the aspiration plunger.
Figure 10:
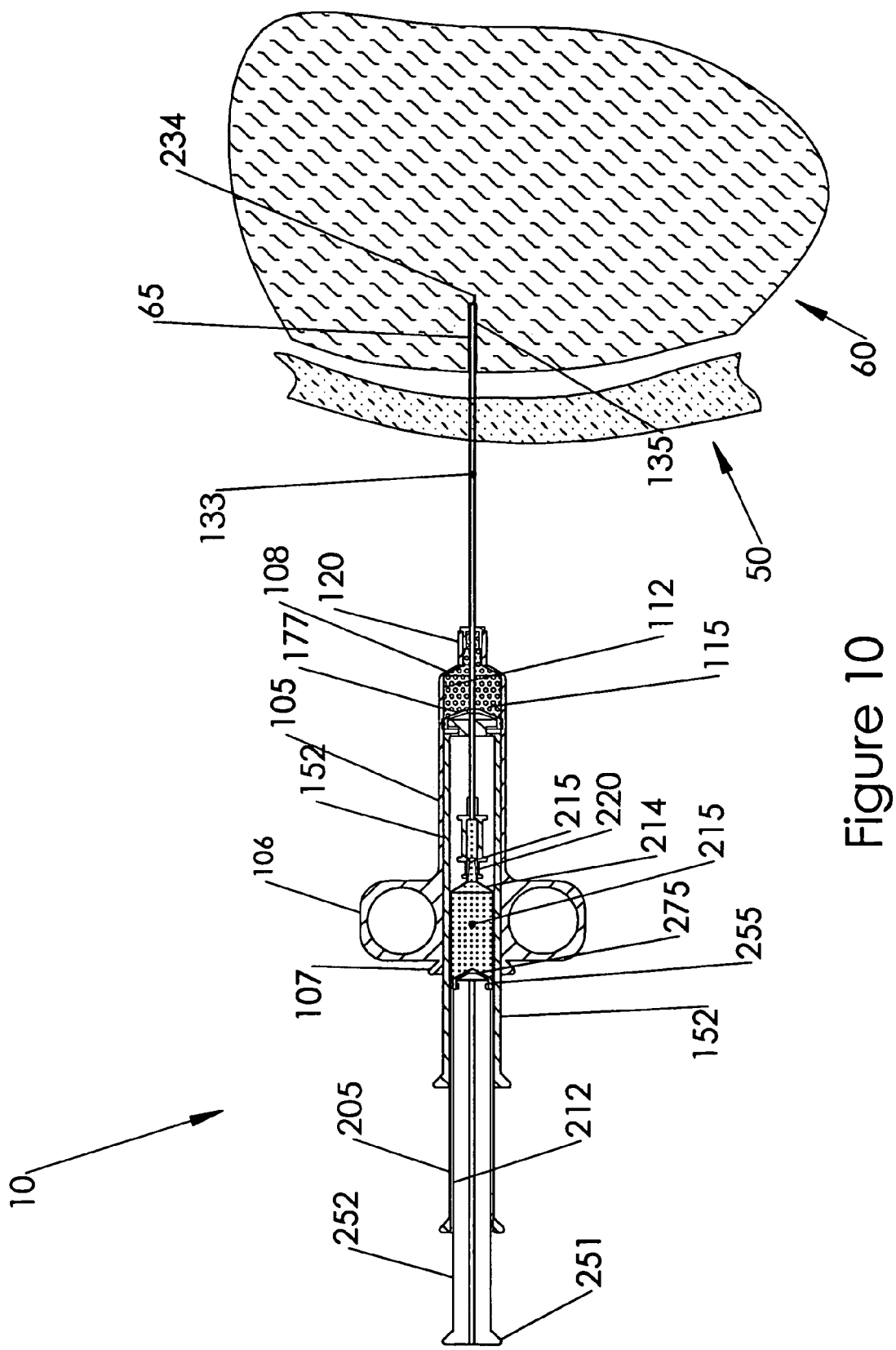
FIG. 10 is a section view of the assembled aspiration device after introduction through the chest wall of a patient and just penetration the organ to be biopsied.
Figure 11:
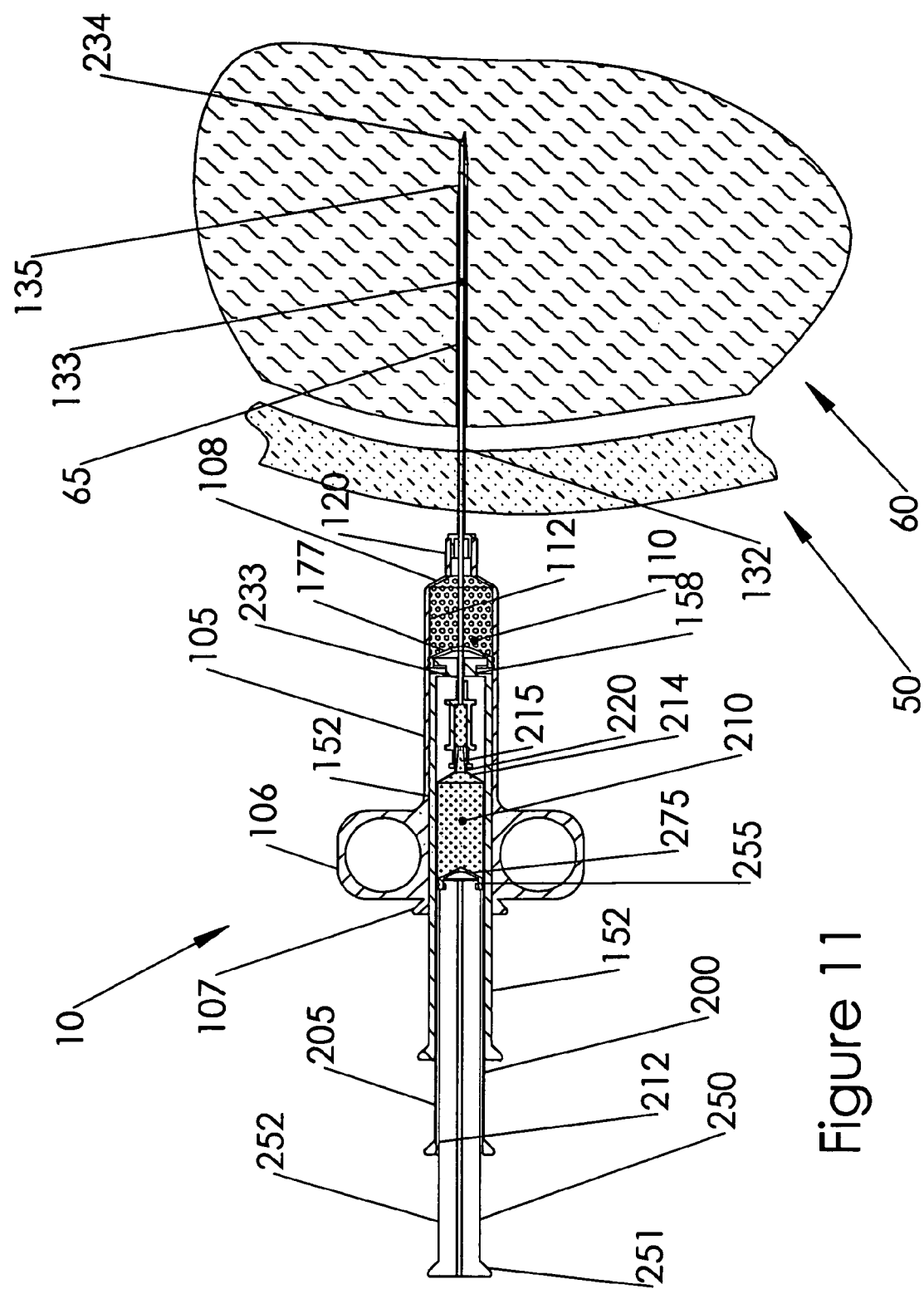
FIG. 11 is a section view of the device penetrating the organ and obtaining a biopsy specimen within the aspiration needle.
Figure 12:
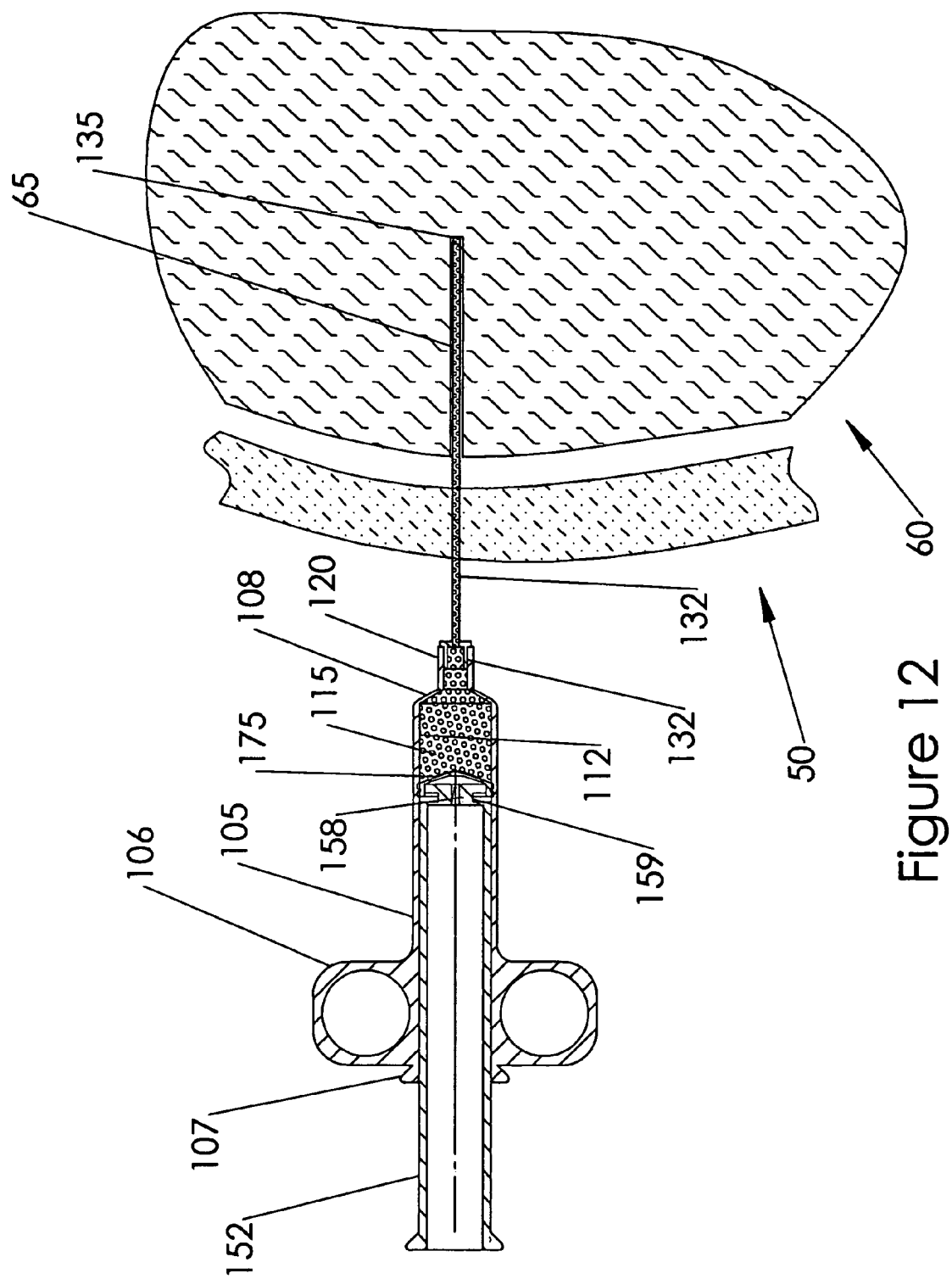
FIG. 12 is a section view of the device after removal of the aspiration syringe and ejection of the application material into the biopsy track after taking a biopsy specimen.
Figure 13:
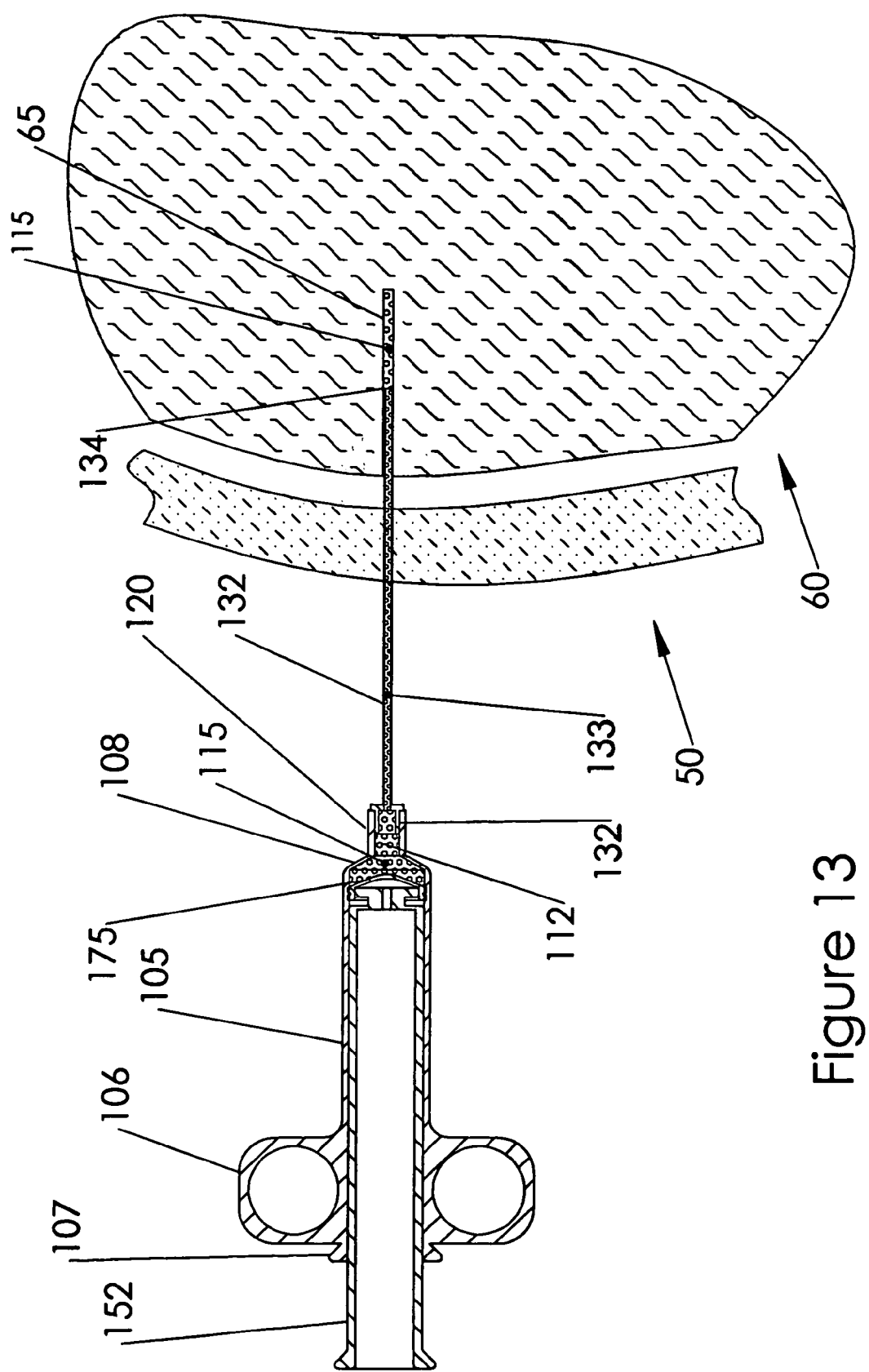
FIG. 13 is a section view of the application syringe being withdrawn and the application material being deposited within the biopsy track.

The syringe plunger 150 of FIG. 4 is a tubular structure with cylindrical walls 152 terminating at an end wall 158. The end wall 158, as seen in detail in FIG. 5, contains a central opening 159 and an attachment member 153 for attaching a rubber plunger 175. The central opening 159 of the disclosed plunger 150 is dimensioned to receive the biopsy needle 230 without binding while preventing excessive movement. Although the illustration of FIG. 5 shows the rubber plunger 175 overlapping the T-shaped attachment member 153, other methods of affixing the rubber plunger 175, or its equivalent, can be use and will be known to those skilled in the art. The plunger 150 is dimensioned to fit into the proximal end of the cylindrical body 100 to establish a fluid seal at the juncture 178 of the plunger 175 and the interior wall 112 of the cylindrical body 105. The plunger 175 has a fluid-chamber face 177, as illustrated in FIG. 5, that establishes a fluid chamber 110 within the syringe barrel 100. Once the biopsy syringe unit, illustrated hereinafter, is inserted into the plunger 150, the biopsy needle 230, of FIG. 6, passes through the fluid chamber 110 and central opening 159, piercing the rubber plunger 175. FIGS. 6–9 exemplifies the biopsy syringe unit consisting of the biopsy needle 230, the plunger 250, and the syringe barrel 200. The biopsy needle 230 is a long cannula 233 with an interior space 235. The distal tip 234 of the cannula 233 is typically cut at an acute angle and an attachment hub 232 at the proximal end is dimensioned for attachment to the syringe barrel 200 at the distal connector hub 220. The biopsy syringe barrel 200, FIG. 7, is typically of a cylindrical structure with walls 205 terminating at the distal wall 214 to form the connecting hub 220 and interior channel 209. The proximal end 207 and interior are dimensioned to receive the biopsy piston 250. The biopsy piston 250 preferably has a distal finger grip end 251, a central body 252 and a distal end 255 for attachment of a rubber plunger 275. The piston 250 after having been fitted into the proximal end 207 of the cylindrical syringe barrel 200 establishes a fluid seal at the juncture of cylindrical side 278 of the plunger 275 and the interior wall 212 of the cylindrical body 205. The distal end 255 of the plunger 275, FIG. 9, has a fluid-chamber face 277 that establishes a fluid chamber 210 within syringe barrel 200.

The outer diameter of the syringe needle 233 is substantially smaller than the diameter of the central opening 159 of plunger 150 to enable the biopsy needle 233 to penetrate and pass through the plunger 175. This creates a slidable fluid seal at the juncture between the plunger 175 and the outer diameter of the needle 230. The outer diameter of the biopsy needle 230 is sufficiently less than the inner diameter of the cannula 132 of the application sheath 130 to enable the biopsy needle 230 to so as to pass through the cannula 132 unobstructed.

The functional and operative position of the syringe apparatus is shown in FIGS. 10 through 13 for a liver biopsy using a coagulant application material. A user-defined volume of coagulant 115, which will be evident to those skilled in the art, is drawn up into the fluid chamber 110 using customary techniques. Likewise, a suitable volume of sterile saline 215 or other fluid is drawn up into the fluid cavity 210 of the biopsy syringe assembly. The apparatus is assembled by inserting the biopsy syringe assembly into the cavity 155 of the application plunger 150 such that the needle 233 passes through the opening 159, plunger 175, the plunger fluid chamber 110, opening 109, and application cannula 130 resulting in the biopsy tip 234 protruding past the cannula end 134.

A suitable spot is identified on the patient and the needle inserted through the chest wall 50 until the capsule of the organ 60 to be biopsied is felt or identified by ultrasound or other means. The assembly is retracted slightly and the biopsy needle 230 flushed with the saline 215 and then inserted into the organ 60, FIG. 10. The biopsy piston 250 is withdrawn slightly creating a negative pressure on the tissue sample within the needle 235. While maintaining the negative pressure, the needle 230 and cannula 132 are advanced into the tissue an appropriate distance, FIG. 11. The biopsy assembly is withdrawn from the application syringe 105 while leaving the application cannula 132 in the biopsy tract 65, FIG. 12. Once the biopsy assembly is withdrawn, the application plunger 150 is depressed injecting the application material 115 into the biopsy track 65 as the cannula tip 134 is withdrawn, FIG. 13.

An alternative method of obtaining a biopsy specimen is the use of a cutting needle biopsy device. FIG. 14 illustrates the assembled cutting device 1000 of another embodiment of the invention. In the illustrated embodiment, the cutting biopsy device 1000 is comprised of a firing mechanism assembly comprising outer cases 420 and 450, which can be separated by a center connecting section 440. The outer cases can also be a single cylindrical unit with the locking components within the case. The proximal end unit 500 contains a movable release unit 550 that, as illustrated in more detail in FIGS. 15 and 16 and described in more detail hereinafter, interacts with the cutting system. Within the outer cases 420 and 450 are internal springs 775 and 875, which apply pressure against the stylet units 700 and 800. A distal end unit 600 connects an outer cannula 850, and a stylet 750 to the stylet units 700 and 800. As with standard cutting biopsy devices, the stylet 750 of the biopsy device 1000 has a specimen trough 775 to catch and retain the tissue specimen after the cannula 850 is rapidly slid over the stylet 750.

The principle of operation of the assembly is exemplified in FIGS. 15 through 20. As shown in FIG. 14, the distal end unit 600 contains a track 610 for alignment with a pin 970 within the plunger 950, as illustrated in FIGS.—23 and 24. The pin 970 must be dimensioned to interact with the track 610. The track 610 begins at the distal end of the distal end unit 600 and proceeds proximally and longitudinally for a prescribed distance A. Once the prescribed distance A is reached, a first, circumferential track 612 is reached which extends around the end unit 600 180 degrees to allow for rotation of the biopsy device 1000 relative to the plunger 950. To fully insert the biopsy device 1000 further into the plunger 950, the device 1000 is rotated 90 degrees from track 610 to place the pin 970 back into alignment with the track 610' and the device 1000 inserted in the plunger 950. Once the biopsy device 1000 is fully inserted, the device 1000 is rotated to place the pin 970 into the proximal, second circumferential track 614 at a prescribed distance B from track 612. The distances A and B are critical to the operation of the disclosed device. When the pin 970 is positioned in the second circumferential track 614, the biopsy device 1000 is in the ready to use position. When the biopsy device 1000 is loaded and ready to use, the pin 970 is placed and rotated fully in the proximal, second circumferential track 614. When in this position, the stylet tip 752 and cannula tip 852 are protruding from the distal tip 921 of the cannula 920. The distance of A and B is approximately equal to the distance C from the distal end 175 of the plunger 950 to the distal tip 921 when the coagulant sheath 920 is properly attached to the syringe 100 with the proper amount of coagulant material 115 drawn into the syringe chamber 110.

Figure 34:
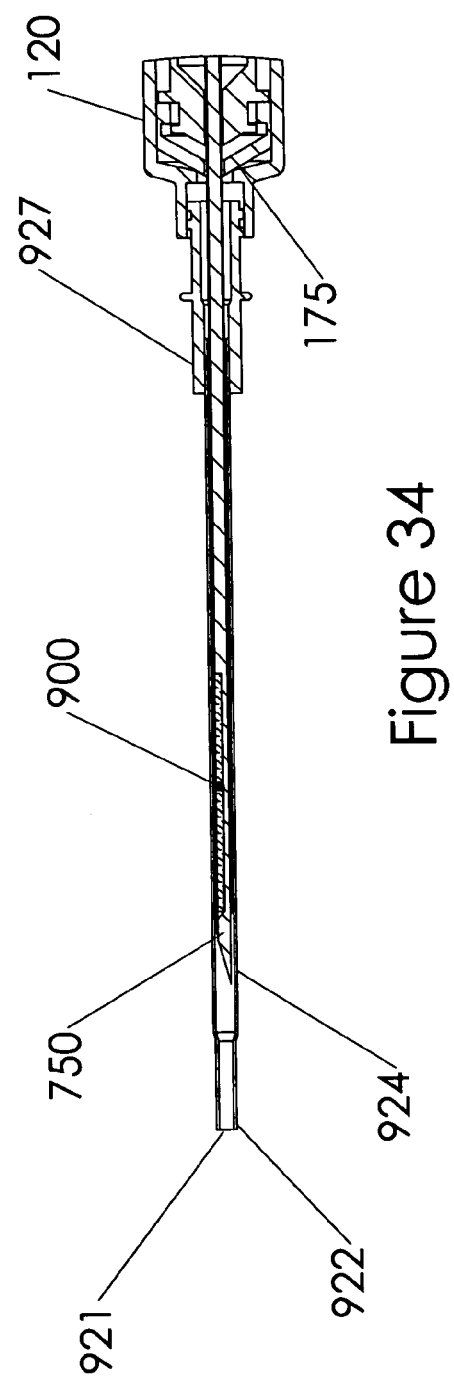
FIG. 34 is a close up of the application sheath with the biopsy specimen enclosed within the stylet and stylet sheath after the application material has been deposited into the biopsy tract.

The second track 614 permits the biopsy device 1000 to be locked in position in order to deliver the coagulant contained in the syringe assembly 100. By locking the biopsy device 100 into position, the user can inject the coagulant without removing the device 1000. To permit the coagulant to flow through the concentric cannula 924, the stylet 750 when in the fired position must be withdrawn past the transition segment 923 plus a distance greater than the distance the rubber seal 175 of plunger 950 is from the distal end 108 of the syringe chamber 110, as shown in FIG. 32. Since the stylet 750 moves with the plunger 950, the stylet 750 must remain clear of the transition segment 923 upon the completion of the coagulant injection, as seen in FIG. 34. If the stylet 750 is within the distal segment 922, the coagulant will be prevented from being ejected.

Figures 35, 36:
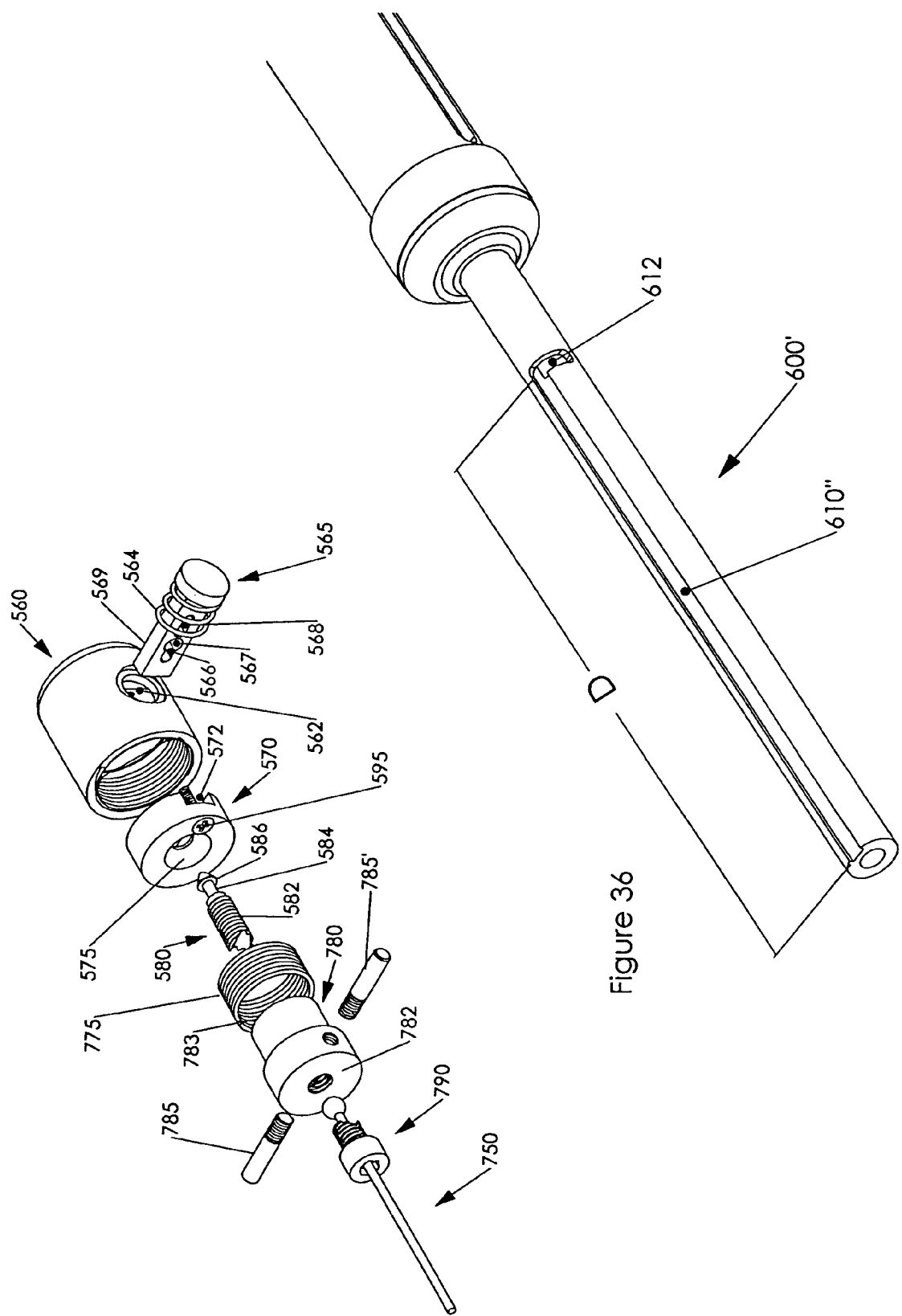
FIG. 35 is a close up of the distal end of the biopsy device showing the single alignment track.
FIG. 36 is an exploded view of an alternative catch and release mechanism for the stylet unit.

Alternatively, distal end unit 610', FIG. 35 can contain only one longitudinal track 610" and one circumferential track 612' located at a distance D approximately equal to the length A+B at which point the biopsy device would need to be totally removed from plunger 950 prior to inserting the coagulant 115. Additionally, markers, such as digital readouts or actual marks on the biopsy device or distal end unit, can be used on the biopsy device to indicated how far to remove the device to enable the coagulant to flow around the stylet.

Figure 15:
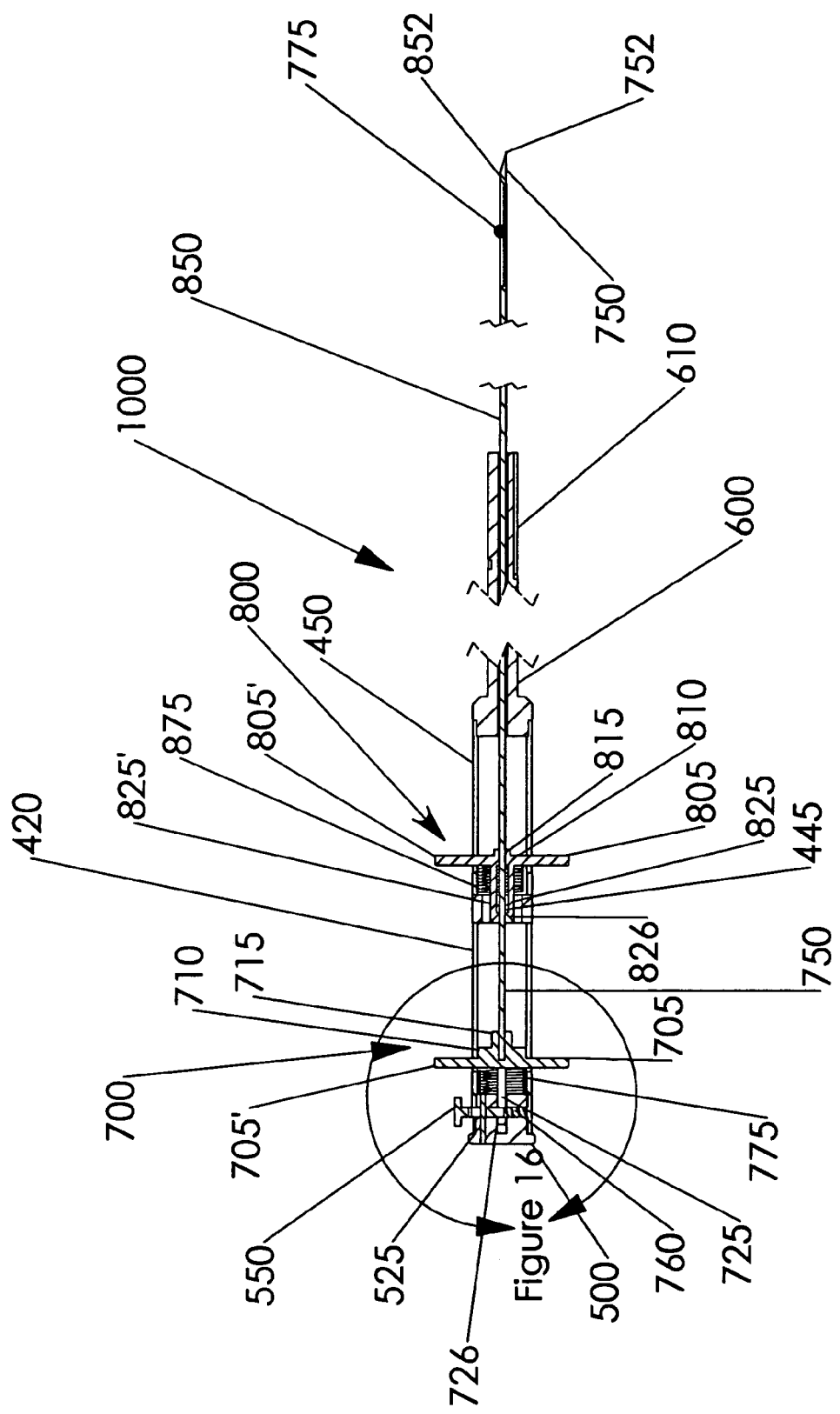
FIG. 15 is a section view of the cutting needle device in the "loaded" or "cocked" position.

The biopsy device as shown in FIG. 15 is in the armed, or ready to use, position whereby the stylet unit 700 is retracted by pulling back, either manually or automatically using an automated device, on pull tabs 705 and 705' towards the end cap 500 compressing the spring 775 to provide the releasable energy to propel the stylet 750 forward into the organ to take the biopsy. Likewise, the cannula unit 800 is retracted by pulling either manually or automatically using an automated device, on pull tabs 805 and 805' towards the crossbar 445 such that the latch fingers 825 and 825' catch on the crossbar 445 preventing the releasable energy of compressed spring 875 from propelling the cannula unit 800 forward.

FIG. 16 details the proximal release mechanism of the device. The flange 553 of release unit 550 catches the latch fingers 726 and 726' of latch arms 725 and 725', respectively, of the stylet unit 700. The latch fingers 726 and 726' prevent the stylet unit 700 from being released when the slide 551 and flange 553 of the release unit 550 are inserted in the slot 503 of the end cap 500. Once in place, the release unit 550 is held in place within the end cap 500 through the use of a pin 525. The pin 525 passes through the end cap hole 502, slot 551 of the release unit 550 and into the hole 502'. The pin 525 prevents the release unit 550 from escaping the end cap 500 due to the spring 760 that maintains the slide 550 in the closed position. When the release unit 550 is manually or by other means depressed, the latch fingers 726, 726' are released from contact with the flange 553 through slots 552 and 552', respectively. The stored energy in spring 775 propels the stylet unit 700 within the case 420 until the front section 715 of holder 710 impacts the latch fingers 825, 825' of the stylet sheath unit 800 such that the stylet trough 775 is extended beyond the distal end of the stylet sheath 850. This is seen in FIGS. 17 and 18 which detail the catch and release mechanism of the stylet sheath unit 800. Upon impact of the front section 715 with the incline surfaces 826 and 826' of latch fingers 825 and 825', the front section 715 forces the latch fingers 825 and 825' to translate outward due to the incline surfaces 826 and 826', respectively. With translation past the width of the crossbar 445, the releasable energy of spring 875 is transferred to kinetic energy and movement of the stylet sheath unit 800 with attached sheath 850 until the front end 815 strikes the distal end unit 600. The stylet sheath unit 800 is translated in a rapid manner distally, as seen in FIG. 19, such that the distal end of sheath 850 cuts the tissue 900 protruding from the trough 775 of stylet 750, FIG. 20, thereby enclosing the tissue specimen.

An alternative catch and release mechanism is shown in FIGS. 36 and 37. In this alternative, the stylet unit 780 provides adjustability for longitudinal positioning of the stylet 750. The stylet is securely positioned in a screw 790 which is longitudinally inserted in the central distal end 782 of unit 780. Pull tabs 785, 785' are secured laterally to unit 780. On the proximal end of unit 780, the catch rod 580 is inserted. The catch rod 580 has a threaded segment 582 that inserts centrally in unit 780 and a catch knob 586 that is restrained by slider 565 after passing through openings 575 of the spacer 570 and circular opening 567 of segment 569 of slider 565 when manually or automatically depressed through opening 562 of end unit 560. When the slider 560 is released, the internal energy of spring 570 forces the slider 560 laterally and entraps the catch knob 586 by means of slot 566 which is of smaller width than the catch knob 586 but greater than the width of catch segment 584. The inclined surface 575 of spacer 570 provides alignment for the catch rod 580 when inserted into the slider 565 and slot 572 provides restraint for slider 560. Screw 595 fastens spacer 570 to end unit 560 after passing through slot 568 thus restraining the lateral movement of slider 565 due to spring 564. Other catch and release mechanisms, as apparent to those in the art, can be employed to employ the operation of the stylet 750 and stylet sheath 850 to obtain a biopsy specimen.

Figure 21:
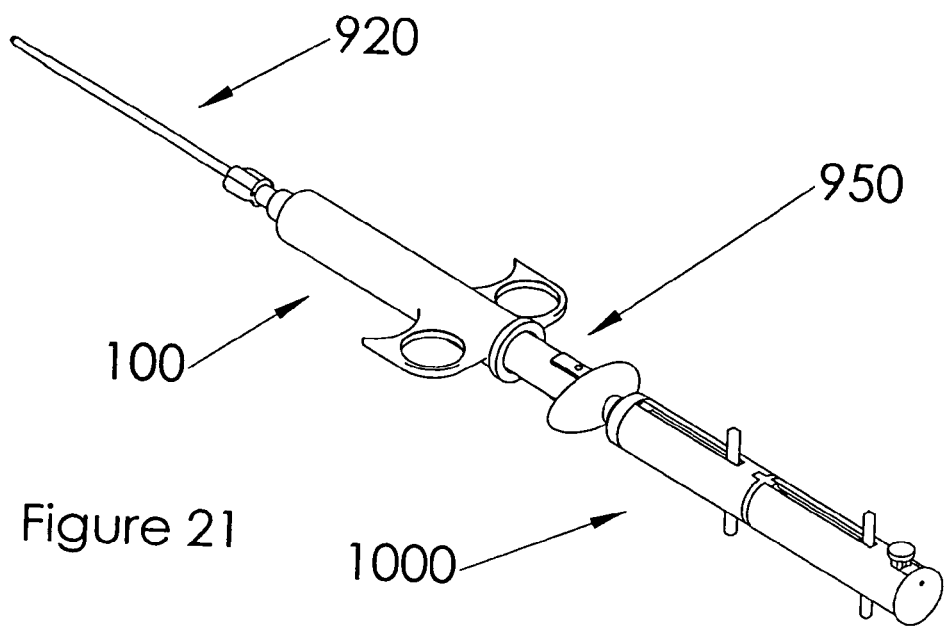
FIG. 21 shows the assembled cutting/application device containing the cutting biopsy device, the application syringe comprised of the syringe barrel, plunger and application cannula.
Figure 22:
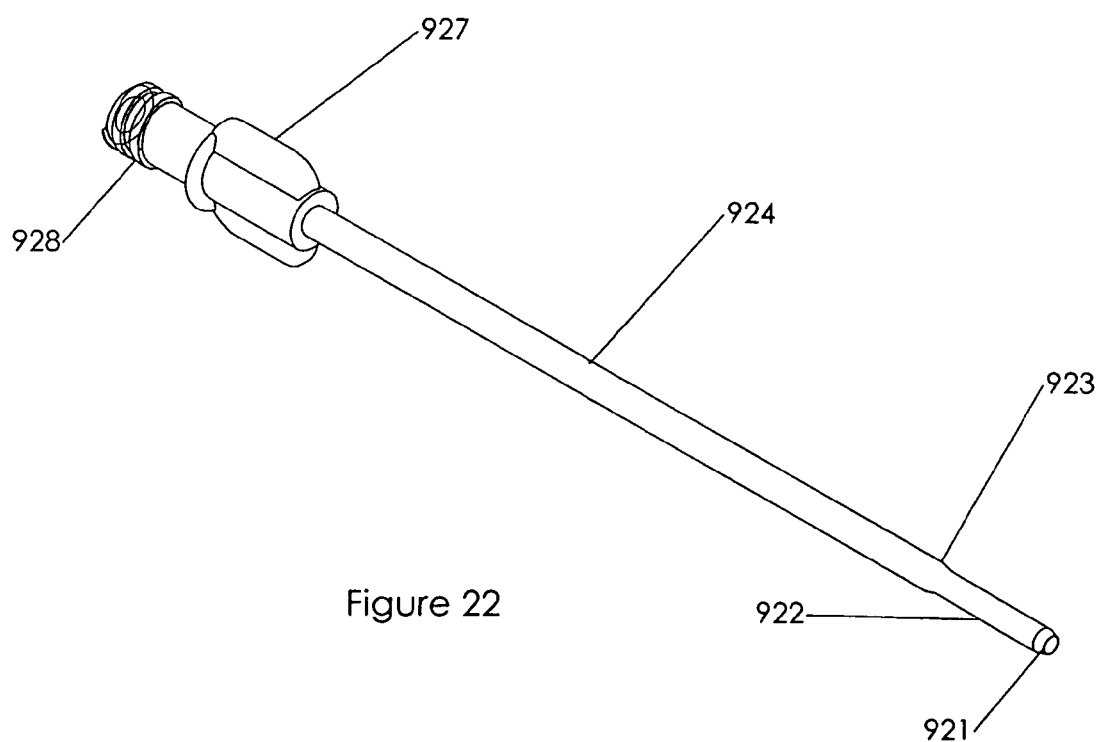
FIG. 22 shows the application cannula comprised of the syringe hub for connecting to the syringe barrel using threaded connection or other customary means and a larger diameter sheath connecting to a smaller diameter sheath at a reducing point and ending at a tapered tip.
Figure 33:
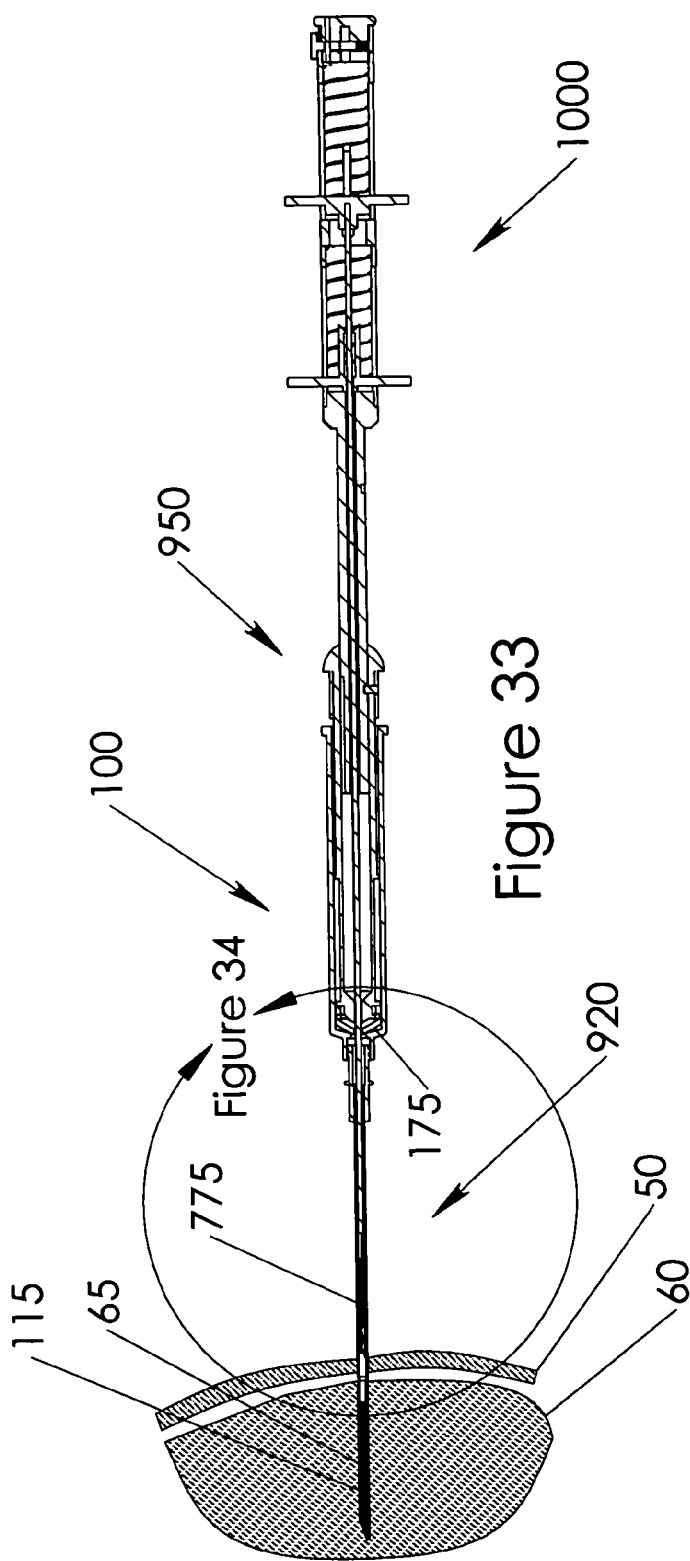
FIG. 33 shows the injection of the application material into the biopsy tract by inserting the application plunger into the application syringe.

FIG. 21 exemplifies the assembled cutting needle/coagulant hemostatic biopsy device incorporating a cutting needle biopsy device 1000 with the delivery syringe 100, plunger 950 and application cannula 920. The application cannula 920, FIG. 22, is connected to the delivery syringe via a threaded or other customary connector on the proximal end of the attachment hub 927. A generally concentric cannula 924 of sufficient length and diameter extends distally from the hub 927. At an appropriate distance the cannula is reduced in diameter at a transition segment 923 to a small diameter distal segment 922 ending in a tapered or beveled tip 921. The internal diameter of the distal segment 921 is dimensioned to permit frictionless passage of the outer cannula 850, while at the same time preventing side-to-side movement.

As seen in more detail in FIGS. 23 and 24, the application plunger 950 is a hollow cylindrical structure 960 having an interior cavity 962, a handle 955 and a distal end 966 for attachment of a plunger seal 175 and central passageway 964. The plunger 950 has an alignment pin 970 inserted through the wall of the structure 960 for mating with the alignment tract 610 to control the displacement of the cutting needle device 1000 relative to the application delivery assembly. The distal end 965 of interior cavity 962 can be tapered to facilitate the insertion of the stylet tip 752 during assembly. The plunger 950 has an optional depth stop 958 to prevent the inadvertent insertion of the plunger 950 into the application syringe 100 but still allow plunger insertion when required. The depth stop 958 is preferably manufactured from a compressible material and has a diameter slightly larger than that of the proximal end of the application syringe 100. The material should have resistance to insertion into the application syringe but, with pressure, have the ability to compress sufficiently to permit insertion.

The operation of the invention with respect to the cutting needle is described FIGS. 25 through 34 which are sectional views of the assembled device of FIG. 21.

The functional and operative position of the cutting/syringe apparatus is shown in FIGS. 25 through 34 for a liver biopsy with a coagulant application material. A user-defined volume of coagulant 115 is drawn up into the fluid chamber 110 (FIG. 11) using customary techniques. The cutting biopsy device 1000 is armed to take a biopsy and inserted into the application assembly 950. The stylet and cannula are inserted from the distal end of the plunger 950 through the cavity 962 (FIG. 24) of the application piston 950 such that the pin 970 follows the alignment track 610 (FIG. 19) and the stylet 750 and sheath 850 (FIG. 20) passes through the opening 964, the plunger seal 175 (FIG. 24), the plunger fluid chamber 110 (FIG. 3), the delivery material 115, opening 109 (FIG. 3) and the application cannula 920 such that the stylet tip 752 and sheath tip 852 protrudes past the cannula end 921. At this point the stylet tip 752 and stylet sheath tip 852 are extended beyond the distal tip of the application cannula 921, FIG. 26, and are penetrating the organ 60 to be biopsied, FIG. 25. The firing button 550 (FIG. 19) is depressed releasing the stylet 700 mechanism as described previously. As the stylet 750 enters the tissue, it causes the tissue to be locally compressed. The tissue then expands and fills the trough 775 distal to the stylet 750. The stylet holder 700 releases the stylet sheath 800 (FIG. 19) from the catch bar 445 (FIG. 18) and is rapidly propelled forward over the stylet 750, as illustrated in FIG. 29. The tissue 900 within the trough 775 is severed and captured by the outer cannula 850, FIG. 30. The cutting device 1000 is rotated and retracted to the intermediate position relative to the plunger 950 using the alignment track 610 as shown in FIG. 31. This intermediate position places the stylet tip 752 of the stylet 750 proximal to the restriction 923 of the application cannula 920, FIG. 32, insuring adequate space between the outer surface of outer cannula 850 and the inner surface of the application cannula 924 for flow of the delivery material 115 through the application cannula 920 when the plunger 950 is depressed into the syringe 100, FIG. 33. The delivery material 115 is then delivered into the biopsy track 65. The biopsy device is removed from the patient, FIG. 34, with the biopsy specimen 900 in the enclosed sheaths. The cutting assembly 1000 is removed and the biopsy specimen 900 retrieved for histological evaluation.

As describe above, the application material can be delivered to the biopsy track through manual operation of the device or the device can be placed in an instrument that automatically manipulates the device to accomplish the required operations.

As described above, the application material can be delivered to the biopsy track by holding the needle sheath 130 stationary and injecting the coagulant through the inner channel 133. According to an alternative embodiment of the invention, the method of delivering the coagulant into the biopsy track can include withdrawing the needle sheath 130 during delivery of the coagulant in an elongated trail that follows the biopsy track. This technique places the absorbable coagulant material in a trail that fills the entire biopsy track and provides the added benefit of providing hemostasis along the entire biopsy track. This is particularly helpful for stopping the bleeding of biopsy tracks in organs that tend to have excessive bleeding such as the liver, kidney, spleen, and other vascular organs.

The device can also be used to deliver a beneficial agent, such as contrast agent, thrombin, radiation treatment, or the like. The applicant material can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Pat. No. 4,619,913, which is incorporated herein by reference.

The present invention can be employed to deliver other materials other than coagulant material into a biopsy track or used to drain and fill an abscess.

While the invention has been described in detail with reference to the preferred embodiments thereof, it will be apparent to one skilled in the art that various changes and modifications can be made and equivalents employed, without departing from the present invention.

What is claimed is:

1. A biopsy assembly for obtaining a tissue specimen and leaving a material in the biopsy track, said device comprising:
    a material delivery device, said material delivery device having:
        a syringe barrel, said syringe barrel having a needle attachment and a delivery material retaining area, a circular needle sheath, said needle sheath attaching to said needle attachment and being in fluid communication with said delivery material retaining area,
a hollow plunger, said hollow plunger being dimensioned to slide within said syringe barrel and having:
a hub at a first end, said hub having an opening dimensioned to receive a biopsy needle and a fluid seal member covering said hub,
an open second end, said open second end being dimensioned to receive at least a portion of a biopsy unit,
a biopsy unit, said biopsy unit having a needle to receive a tissue specimen, said needle being concentric with said needle sheath and having a diameter less than said needle sheath.

2. The assembly of claim 1 wherein said biopsy unit is an aspiration biopsy unit for obtaining a biopsy specimen using an aspiration needle greater than the combined length of said needle sheath, needle attachment, delivery material chamber and fluid seal member of said material delivery device.

3. The assembly of claim 1 wherein said biopsy unit has a body, a stylet and a cutting needle, said cutting needle and said stylet being dimensioned to fit within said needle sheath.

4. The assembly of claim 3 wherein said material delivery device further comprises a distance guide, said distance guide extending into said hollow plunger.

5. The assembly of claim 4 wherein said distance guide is a pin.

6. The assembly of claim 4 wherein said distance guide is an electromechanical sensing unit.

7. The assembly of claim 3 wherein said biopsy unit further comprises a reference guide, said reference guide being at a distal end of said body and interacting with said distance guide.

8. The assembly of claim 7 wherein said reference guide is a track, said track being dimensioned to receive said distance guide.

9. The assembly of claim 3 wherein said needle sheath has a proximal diameter and a distal diameter, said distal diameter being less than said proximal diameter.

10. The assembly of claim 8 wherein said stylet and said cutting needle are within said proximal diameter upon injection of said delivery material.

11. A biopsy assembly for obtaining a tissue specimen and leaving a material in the biopsy track, said device comprising:
a material delivery device, said material delivery device having
a syringe barrel, said syringe barrel having a needle attachment and a delivery material retaining area,
a needle sheath, said needle sheath attaching to said needle attachment and having a proximal diameter and a distal diameter, said distal diameter being less than said proximal diameter,
a hollow plunger, said hollow plunger being dimensioned to slide within said syringe barrel and having:
a distance guide, said distance guide extending into said hollow plunger,
a hub at a first end, said hub having an opening dimensioned to receive a biopsy needle and a fluid seal member covering said hub,
an open second end, said open second end being dimensioned to receive at least a portion of a biopsy unit.

12. The assembly of claim 10 further comprising a biopsy unit having:
a body, said body having a needle release system at a first end and a reference guide at a second end of said body, said reference guide being dimensioned to fit within said hollow plunger to interact with said distance guide to indicate a predetermined biopsy needle tip placement,
a cutting mechanism, said cutting mechanism being dimensioned to fit within said distal diameter of said needle sheath.

13. The assembly of claim 12 wherein said distance guide is a pin within said hollow plunger and said reference guide is a track dimensioned to receive said pin.

14. The assembly of claim 13 wherein said track is straight.

15. The assembly of claim 13 wherein said track is curved.

16. The assembly of claim 13 wherein said track starts at a first position at the distal end of said body, proceeds toward a proximal end on a longitudinal track for a first predetermined longitudinal distance, changes to a circumferential track for a first predetermined circumferential distance, proceeds on a second longitudinal track toward said proximal end for a second predetermined longitudinal distance, changes to a second circumferential track for a second predetermined circumferential distance, proceeds on a third longitudinal track for a third predetermined longitudinal distance, said longitudinal track being dimensioned to receive said guide pin.

17. The assembly of claim 16 wherein said first circumferential track continues circumferentially beyond said second longitudinal track to create a lock port to enable a user to lock said biopsy unit in relationship to said material delivery device.

18. The assembly of claim 17 wherein placement of said pin in said lock port places the distal end of said cutting mechanism within said needle sheath first diameter after injection of said material.

* * * * *